United States Patent
Helal

(10) Patent No.: US 11,124,522 B2
(45) Date of Patent: Sep. 21, 2021

(54) CHEMOSENSOR AND A METHOD OF DETECTING PALLADIUM IONS

(71) Applicant: King Fahd University of Petroleum and Minerals, Dhahran (SA)

(72) Inventor: Aasif Helal, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 16/439,238

(22) Filed: Jun. 12, 2019

(65) Prior Publication Data

US 2020/0392148 A1 Dec. 17, 2020

(51) Int. Cl.
C07D 491/107 (2006.01)
G01N 21/33 (2006.01)
G01N 21/64 (2006.01)
G01N 31/22 (2006.01)

(52) U.S. Cl.
CPC ......... *C07D 491/107* (2013.01); *G01N 21/33* (2013.01); *G01N 21/6428* (2013.01); *G01N 31/22* (2013.01)

(58) Field of Classification Search
CPC .............. C07D 491/107; G01N 21/33; G01N 21/6428; G01N 31/22
See application file for complete search history.

(56) References Cited

U.S. PATENT DOCUMENTS

2017/0276607 A1* 9/2017 Helal .................... G01N 33/582
2018/0194944 A1 7/2018 Helal

FOREIGN PATENT DOCUMENTS

CN 108456514 A 8/2018

OTHER PUBLICATIONS

"Fluorescein-N-Methylimidazole conjugate as Cu2+ sensor in mixed aqueous media through electron transfer." Journal of fluorescence 26.1 (2016): 1-9 (Year: 2016).*
Fluorescein derived Schiff base as fluorimetric zinc (II) sensor via 'turn on' response and its application in live cell imaging. Spectrochimica Acta Part A: Molecular and Biomolecular Spectroscopy 212 (2019): 222-231. (Year: 2019).*

(Continued)

*Primary Examiner* — Lyle Alexander
*Assistant Examiner* — Oyeleye Alexander Alabi
(74) *Attorney, Agent, or Firm* — Oblon, McClelland, Maier & Neustadt, L.L.P.

(57) ABSTRACT

A palladium selective chemosensor based on a fluorescein-allyloxy benzene scaffold and a method of detecting palladium ions in a fluid sample with the chemosensor, whereby the fluid sample is contacted with a solution that includes water and the chemosensor to form a mixture. An ultraviolet visible absorption profile and/or a fluorescence emission profile of the mixture is measured to determine a presence or absence of palladium ions in the fluid sample, wherein the chemosensor has an ultraviolet visible absorption peak at 315 to 325 nm and a fluorescence emissions peak at 380 to 400 nm in the solution, and wherein a bathochromic shift in the ultraviolet visible absorption peak to 338 to 342 nm in the mixture and/or a bathochromic shift in the fluorescence emissions peak to 530 to 550 nm in the mixture indicates the presence of palladium ions in the fluid sample.

20 Claims, 8 Drawing Sheets

(56) References Cited

OTHER PUBLICATIONS

Zhang, J., Zhang, L., Zhou, Y. et al. A highly selective fluorescent probe for the detection of palladium(II) ion in cells and aqueous media. Microchim Acta 180, 211-217 (2013). https://doi.org/10.1007/s00604-012-0922-2]: (Year: 2013).*

Helal, Aasif. "Sequential detection of palladium and chromium oxyanion by a fluorescein based chemosensor in mixed aqueous media." Chemosensors 8.1 (2020): 4. (Year: 2020).*

Das, et al. ; Fluorescein derived Schiff base as fluorimetric zinc (II) sensor via 'turn on' response and its application in live cell imaging ; Spectrochimica Acta Part A: Molecular and Biomolecular Spectroscopy, vol. 212 ; pp. 222-231 ; Apr. 5, 2019 ; Abstract Only ; 3 Pages.

Zhang, et al. ; A selectively fluorescein-based colorimetric probe for detecting copper(II) ion ; Spectrochimica Acta Part A: Molecular and Biomolecular Spectroscopy, vol. 133 ; pp. 54-59 ; Dec. 10, 2014 ; Abstract Only ; 2 Pages.

Li et al. Fluorescent Probes for Pd Detection by Allylidene-Hydrazone Ligands with Excellent Selectivity and Large Fluorescence Enhancement ; Cehmistry—A European Journal, vol. 16, Issue 41 ; Sep. 17, 2010 ; Abstract Only ; 12 Pages.

Kitley, et al. ; Synthesis of High Contrast Fluorescein-Diethers for Rapid Bench-Top Sensing of Palladium ; The Royal Society of Chemistry 2015 ; 12 Pages.

\* cited by examiner

Reagents and conditions: (i) NH₂NH₂, MeOH, reflux; (ii) EtOH, reflux; (iii) Allyl bromide, K₂CO₃, CH₃CN, reflux.

CHEMOSENSOR AND A METHOD OF DETECTING PALLADIUM IONS

BACKGROUND OF THE INVENTION

Field of the Invention

The present invention relates to a palladium selective chemosensor, particularly a chemosensor based on a fluorescein-allyloxy benzene scaffold, and methods of detecting palladium ions in a fluid sample with the chemosensor.

DISCUSSION OF THE BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Fluorescent chemosensor technology for sensing and monitoring heavy and transitional metal ions (HTM) is an attractive field due to its high sensitivity and simplicity. See Quang D T, Kim J S (2010) Chem Rev 110: 6280-6301; and Kim H N, Ren W, Kim J S, Yoon J (2012) Chem Soc Rev 41: 3210-3244, each incorporated herein by reference in their entirety. Palladium is a transition metal that belongs to the platinum-group elements (PGEs). It plays a significant role in chemical transformations and acts as a catalyst in reactions such as the Buchwald-Hartwig, Heck, Sonogashira, Suzuki-Miyaura, hydrogenation and dehydrogenation reactions that are widely used to make complex molecules in the pharmaceuticals industries. See Liu C, Zhang S K, Zhang Y X, Jin Z L (2015) Chin Chem Lett 26: 55-57; Tietze L F, Ila H, Bell H P (2004) Chem Rev 104: 3453-3516; and Amini M, Bagherzadeh M, Rostamnia S (2013) Chin Chem Lett 24: 433-436, each incorporated herein by reference in their entirety. Palladium is also extensively used as an important component in various materials such as alloys, dental crowns, fine jewelry and fuel cells. See Lyons T W, Sanford M S (2010) Chem Rev 110:1147-1169; and Lafrance M, Fagnou K (2006) J Am Chem Soc 128:16496-16497, each incorporated herein by reference in their entirety. Palladium is also employed in high-tech fields such as navigation, aviation, and the automotive industry especially in automobile catalytic converters. See Alt F, Zereini, F Springer-Verlag, Berlin, 2006, incorporated herein by reference in its entirety. The increased use of palladium inevitably leads to increased emission of palladium into the environment, and because palladium is non-biodegradable, it can accumulate in the food chain and result in serious health hazards due to degradation of DNA and cell mitochondria, and also enzyme inhibition. For example, palladium can bind to thiol-containing proteins (silk fibroin, casein, and many enzymes), amino acids, DNA, and other macromolecules (vitamin $B_6$) that leads to disturbance in a variety of cellular processes. See Li H, Fan J, Peng X (2013) Chem Soc Rev 42: 7943-7962, incorporated herein by reference in its entirety. Thus, the proposed maximum dietary intake for this ubiquitous and poisonous heavy metal is less than 1.5-15 μg per person per day and its threshold in drugs is 5-10 ppm. See Wang J, Song F, Wang J, Peng X (2013) Analyst 138: 3667-3672, incorporated herein by reference in its entirety.

Traditional analytical techniques used for the detection of palladium include atomic absorption/emission spectroscopy (AAS), solid-phase microextraction high performance liquid chromatography (SPME-HPLC), inductively coupled plasma atomic emission spectroscopy (ICP-AES), time-of-flight resonance ionization mass spectrometry, capillary zone electrophoresis, and X-ray fluorescence, etc. However, all of these methods need expensive facilities, complicated sample-pretreatment procedures and well-controlled, rigorous experimental conditions. See Meel K V, Smekens A, Behets M, Kazandjian P, Grieken R V (2007) Anal Chem 79: 6383-6389; and Dimov S S, Chryssoulis S L, Lipson R H (2003) Anal Chem 75: 6723-6727, each incorporated herein by reference in their entirety. Thus a convenient, highly sensitive, selective and expeditious method for the analysis of palladium is still needed.

Recently, optical (colorimetric and fluorescent) chemosensors (or simply chemosensors) have attracted attention due to their high selectivity, sensitivity, operational simplicity, rapidity and nondestructive nature. See Carter K P, Young A M, Palmer A E (2014) Chem Rev 114: 4564-4601; Huo B, Du M, Gong A, Li M, Fang L, Shen A, Lai Y, Bai X, Yang Y (2018) Anal Methods (Advance article); and Che C, Chen X, Wang H, Li JQ, Xiao Y, Fu B, Qin Z (2018) New J Chem (Advance article), each incorporated herein by reference in their entirety. One strategy to synthesize palladium sensors is to use palladium catalyzed reactions such as Pd-catalyzed cyclization for the formation of pyrone, pyrrole, and oxazole, Pd-catalyzed depropargylation reactions and deallylation reactions, the Pd-catalyzed Heck, and the Suzuki-Miyaura coupling reactions. See Jun M E, Ahn K H (2010) Org Lett 12: 2790-2793; Pershagen E, Nordholm J, Borbas, K E (2012) J Am Chem Soc 134: 9832-9835; Balamurugan R, Chien C C, Wu K-M, Chiu Y-H, Li J-H (2013) Analyst 138: 1564-1569; Song F, Garner A L, Koide, K. (2007) J Am Chem Soc 129, 12354-12355; Yu S, Rhee, H-W, Hong J-I (2011) Tetrahedron Lett 52: 1512-1514; and Yusop R M, Unciti-Broceta A, Johansson E M V, Sanchez-Martin R M, Bradley M (2011) Nat Chem 3: 239-243, each incorporated herein by reference in their entirety. Several fluorescent quenching chemosensors based on the ICT (Intramolecular Charge Transfer) mechanism for palladium have also been designed. See Ashwina B C M A, Sivaraman G, Stalina T, Yuvakkumar R, Mareeswarana P M (2018) J Photochem Photobiol B 183: 302-308, incorporated herein by reference in its entirety. However, many of these chemosensors still have impediments such as interference from other metal ions, insolubility in water, the need for additional reagents for analysis, and laborious synthesis processes with expensive chemicals.

A valuable bioimaging analysis in vivo depends on the sensitivity and selectivity of the chemosensor, as well as on the concentration of the analyte and the chemosensor. In a cellular environment, the chemosensor concentration depends on many factors such as membrane permeability, incubation temperature and time, change in the cell size and phototransformation. The chemosensor concentration in turn controls the fluorescence intensity modulation of a system. See Srikun D, Miller E W, Domaille D W, Chang C J. (2008) J Am Chem Soc 130: 4596-4597, incorporated herein by reference in its entirety. Such drawbacks can be overcome by using ratiometric chemosensors. These chemosensors also eliminate other complications by self-calibration of two emission bands and can also expand the dynamic range of fluorescence measurement. Moreover, with the advancement of two-photon microscopy imaging, a new generation of ratiometric chemosensors, which produce large shifts of the emission energy upon binding with the analyte, is also required. See Zhou Z, Yu M, Yang H, Huang K, Li F, Yi T, Huang C (2008) Chem Commun 3387-3389, incorporated herein by reference in its entirety. Some of the common mechanisms designed to produce ratiometric changes are ICT (Intramolecular Charge Transfer), FRET (Fluorescence Resonance Energy Transfer), CHEF (Chelation-Enhanced Fluorescence), the pyrene monomer-excimer transformation, and ESIPT (Excited State Intramolecular Proton Transfer). See Wang Y, Shu W, Han B, Zhao X, Wu L, Liu C, Ma Z, Zhu B, Du B (2017) New J Chem 41: 9262-9267; Vinkenborg J L, Nicolson T J, Bellomo E A, Koay M S, Rutter G A, Merkx M (2009) Nat. Methods 6: 737-740; Kar C, Adhikari M D, Datta B K, Ramesh A, Das G (2013) Sens Actuator B-Chem 188:1132-1140; Tang L, Wu D, Wen X, Dai X, Zhong K (2014) Tetrahedron 70: 9118-9124; and Wu J, Liu W, Ge J, Zhang H, Wang P (2011) Chem Soc Rev 40: 3483-3495, each incorporated herein by reference in their entirety. The two fluorophore approach, conformational restriction, the self-assembly strategy and the chemodosimeter approach through irreversible chemical reactions are some of the mechanisms employed. See Woodroofe C C, Lippard S J (2003) J Am Chem Soc 125: 11458-11459; Ajayaghosh A, Carol P, Sreejith S (2005) J Am Chem Soc 127: 14962-14963; Wu Z, Zhang Y, Ma J S, Yang G (2006) Inorg Chem 45: 3140-3142; and Jiang J, Jiang H, Liu W, Tang X, Zhou X, Liu W, Liu R (2011) Org Lett 13: 4922-4925, each incorporated herein by reference in their entirety.

Xanthene (fluorescein and rhodamine) based chemosensors are very efficient fluorescent chemosensors as they can be (a) easily synthesized and functionalized; (b) their excitation and emission wavelengths lie in the visible region; (c) they also have a high fluorescence quantum yield, molar extinction coefficient, photostability and water solubility; and (d) they are biocompatible. See Zheng H, Zhan X-Q, Biana Q-N, Zhanga X-J (2013) 49: 429-447; Chen X, Pradhan T, Wang F, Kim J S, Yoon J (2011) Chem Rev 112: 1910-1956; Xiong X Q, Song F L, Chen G W, Sun W, Wang J Y, Gao P (2013) Chem Eur J 19: 6538-6545; and An J M, Yan M H, Yang Z Y, Li T R, Zhou Q X (2013) Dyes Pigments 99: 1-5, each incorporated herein by reference in their entirety. Moreover, xanthene-based chemosensors are beneficial in terms of their switch on-off type chemosensors due to the conversion of a spirolactam (nonfluorescent) to ring-opened amide (fluorescent) structure. See Jua H, Lee M H, Kim J, Kim J S, Kim J (2011) Talanta 83: 1359-1363, incorporated herein by reference in its entirety. The presence of heteroatoms such as oxygen, nitrogen, phosphorus, and sulfur within the xanthene ring helps in the binding of soft metal ions like palladium. See Wang M, Liu X, Lu H, Wang H, Qin Z (2015) ACS Appl Mater Interfaces 7: 1284-1289, incorporated herein by reference in its entirety. But traditional xanthene-based chemosensors suffer from the interference of other metal ions, and also the pH-sensitive fluorescein or rhodamine fluorophore may introduce detection errors into the results.

In view of the forgoing, there is a need for effective, sensitive, and selective ratiometric chemosensors for the detection of palladium, which are easy and inexpensive to make, and which are can operate under a broad range of pH values.

SUMMARY OF THE INVENTION

Accordingly, it is one object of the present invention to provide ratiometric and chemodosimetric chemosensors based on a fluorescein-allyloxy benzene scaffold for the detection of palladium ions, which provide easily identifiable on-off optical readouts, are highly sensitive to and are selective for only palladium ions, are easy to make, and which can operate under a broad range of pH values.

It is another object of the present disclosure to provide methods of making and using the fluorescein-allyloxy benzene type chemosensors for the detection of palladium and/or determination of palladium ion concentration in a fluid sample.

Thus the present disclosure provides:

A method of detecting palladium ions in a fluid sample involving contacting the fluid sample with a solution comprising water and a chemosensor to form a mixture, and measuring an ultraviolet visible absorption profile and/or a fluorescence emission profile of the mixture to determine a presence or absence of palladium ions in the fluid sample, wherein the chemosensor is of formula I

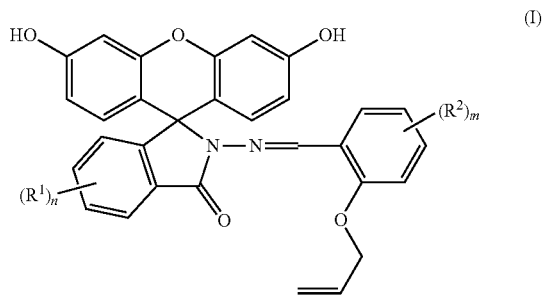

wherein:
each $R^1$ is independently an optionally substituted alkyl, an optionally substituted alkoxy, a carboxy, a disubstituted amino, an alkanoylamino, an amido, or an isothiocyano,
each $R^2$ is independently an optionally substituted alkyl, an optionally substituted aryl, an optionally substituted alkoxy, an alkanoyloxy, an optionally substituted alkoxycarbonyl, a halo, a substituted amino, a nitro, a cyano, or an azo,
n is 0 to 2, and
m is 0 to 4.

In some embodiments, n +m is equal to 0 to 2.

In some embodiments, n is 0, or n is 1 and $R^1$ is an optionally substituted alkyl or an optionally substituted alkoxy.

In some embodiments, m is 0, or m is 1 and $R^2$ is an optionally substituted alkyl, an optionally substituted alkoxy, or a halo.

In some embodiments, the chemosensor of formula I is

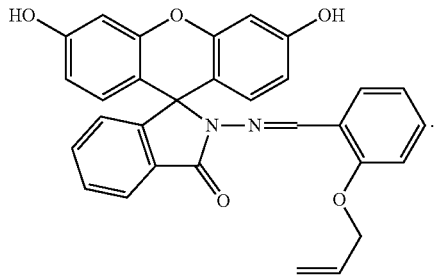

In some embodiments, the chemosensor of formula I is present in the mixture at a concentration of 0.1 to 20 μM, based on a total volume of the mixture.

In some embodiments, palladium ions are present in the fluid sample, and a molar equivalence of the palladium ions to the chemosensor of formula I in the mixture is from 0.05:1 to 20:1.

In some embodiments, the solution further includes an organic solvent, and a ratio of water to the organic solvent in the solution is from 5:1 to 20:1.

In some embodiments, the solution further includes 1 to 50 mM of a buffer, based on a total volume of the solution, and the mixture has a pH of 5 to 9.

In some embodiments, the buffer is 4-(2-hydroxyethyl)-1-piperazineethanesulfonic acid.

In some embodiments, the fluid sample includes greater than 55% v/v of water, and the fluid sample is an industrial wastewater or a bodily fluid.

In some embodiments, the solution is contacted with the fluid sample for 1 second to 10 minutes prior to the measuring.

In some embodiments, the chemosensor of formula I has an ultraviolet visible absorption peak at 315 to 325 nm and a fluorescence emissions peak at 380 to 400 nm in the solution, and wherein a bathochromic shift in the ultraviolet visible absorption peak to 338 to 342 nm in the mixture and/or a bathochromic shift in the fluorescence emissions peak to 530 to 550 nm in the mixture indicates the presence of palladium ions in the fluid sample.

In some embodiments, the fluorescence emission profile of the mixture is measured, and the method further involves determining a concentration of the palladium ions in the fluid sample by measuring a fluorescence intensity ratio of the mixture at 540 nm and 390 nm ($I_{540}/I_{390}$), and comparing to a calibration curve that relates palladium ion concentration to the fluorescence intensity ratio ($I_{540}/I_{390}$).

In some embodiments, the fluid sample includes one or more cations of sodium, potassium, calcium, magnesium, strontium, rubidium, cesium, iron, cobalt, copper, nickel, zinc, cadmium, mercury, silver, aluminum, gallium, and lead.

In some embodiments, the method is selective for the detection of palladium ions, wherein only the presence of palladium ions in the mixture produces a bathochromic shift in the ultraviolet visible absorption profile and/or the fluorescence emission profile of the mixture.

In some embodiments, the method has a palladium ion detection lower limit of 40 to 60 ppb.

The present disclosure also provides a chemosensor of formula I,

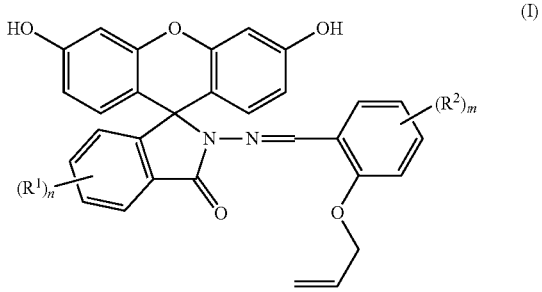

(I)

wherein:

each $R^1$ is independently an optionally substituted alkyl, an optionally substituted alkoxy, a carboxy, a disubstituted amino, an alkanoylamino, an amido, or an isothiocyano, each $R^2$ is independently an optionally substituted alkyl, an optionally substituted aryl, an optionally substituted alkoxy, an alkanoyloxy, an optionally substituted alkoxycarbonyl, a halo, a substituted amino, a nitro, a cyano, or an azo, n is 0 to 2, and
m is 0 to 4.

In some embodiments, n + m is equal to 0 to 2.

In some embodiments, the chemosensor of formula I is

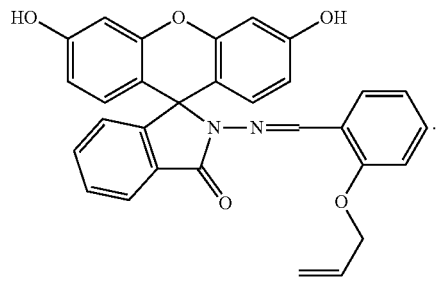 [SMILES: C=CCOc1ccccc1C=NN1C(=O)c2ccccc2C12c1ccc(O)cc1Oc1cc(O)ccc12]

BRIEF DESCRIPTION OF THE DRAWINGS

The foregoing paragraphs have been provided by way of general introduction, and are not intended to limit the scope of the following claims. A more complete appreciation of the invention and many of the attendant advantages thereof will be readily obtained as the same becomes better understood by reference to the following detailed description when considered in connection with the accompanying drawings, wherein:

DETAILED DESCRIPTION OF THE INVENTION

Figure 1A:
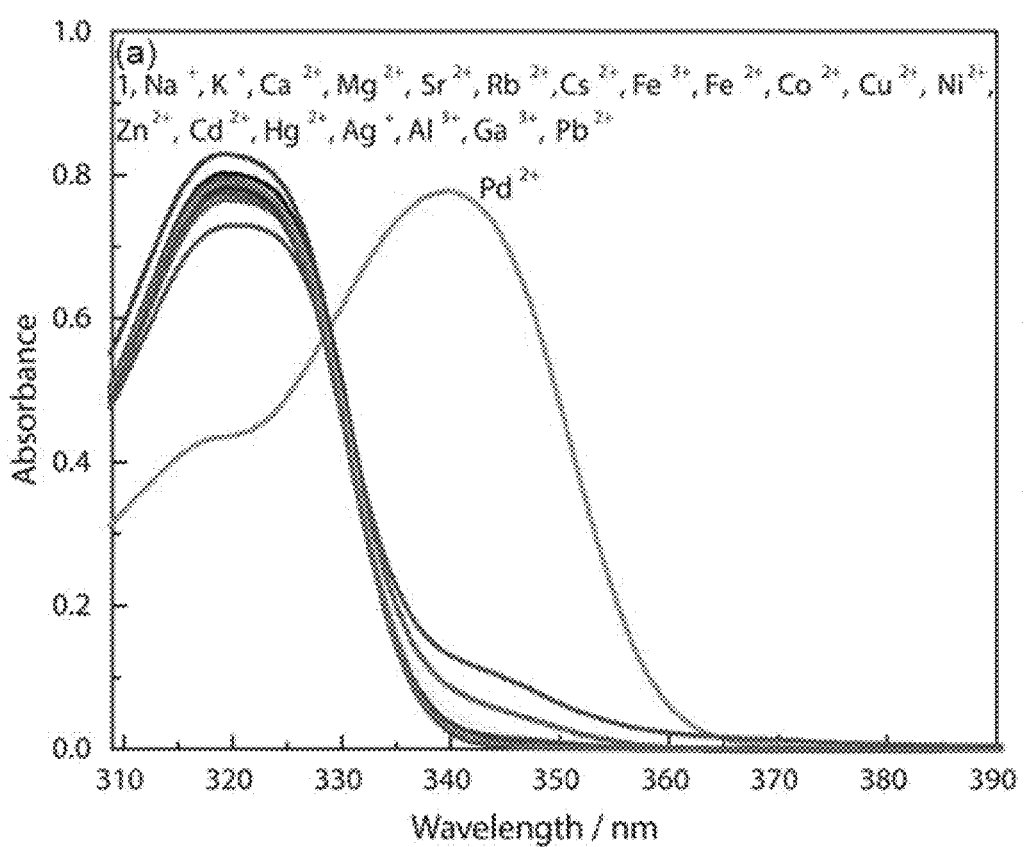
FIGS. 1A-1C illustrate the UV-Vis spectra of 1 (10 μM) with different cations (10 equivalents) (FIG. 1A), upon the addition of PdCl$_2$ in different equivalence (up to 100 μM) in H$_2$O:DMF (9:1) containing HEPES buffer (10 mM, pH 7.4) (FIG. 1B), and as a mol ratio (equiv. Pd$^{2+}$) plot of absorbance at 340 nm (FIG. 1C)

In the following description, it is understood that other embodiments may be utilized and structural and operational changes may be made without departure from the scope of the present embodiments disclosed herein.

Definitions

As used herein, "wastewater" means a water source obtained from storm drains, sedimentation ponds, runoff/outflow, landfills, as well as water sources resulting/obtained from industrial processes such as factories, mills, farms, mines, quarries, industrial drilling operations, oil and gas recovery operations, pharmaceutical processes, papermaking processes, food preparation processes, phase separation processes, washing processes, waste treatment plants, toilet processes, power stations, incinerators, spraying and painting, navigation processes, aviation processes, automotive plants, fuel cell manufacturing operations, or any other manufacturing or commercial enterprise, which comprises water and one or more compounds or materials derived from such industrial processes, including partially treated water from these sources.

As used herein, the term "fatty" describes a compound with a long-chain (linear) hydrophobic portion made up of hydrogen and anywhere from 6 to 26, 8 to 24, 10 to 22, 12 to 20, 14 to 18 carbon atoms, which may be fully saturated or partially unsaturated, and optionally attached to a polar functional group such as a hydroxyl group, an amine group, or a carboxyl group (e.g., carboxylic acid). Fatty alcohols, fatty amines, fatty acids, fatty esters, and fatty amides are examples of materials which contain a fatty portion, and are thus considered "fatty" compounds herein.

As used herein, "alkoxylated" or "alkoxylate" refers to compounds containing a (poly)ether group (i.e., (poly)oxyalkylene group) derived from reaction with, oligomerization of, or polymerization of one or more alkylene oxides having 2 to 4 carbon atoms, and specifically includes (poly)oxyethylene (derived from ethylene oxide, EO), (poly)oxypropylene (derived from propylene oxide, PO), and (poly)oxybutylene (derived from butylene oxide, BO), as well as mixtures thereof.

The phrase "substantially free", unless otherwise specified, describes a particular component being present in an amount of less than about 1 wt. %, preferably less than about 0.5 wt. %, more preferably less than about 0.1 wt. %, even more preferably less than about 0.05 wt. %, yet even more preferably 0 wt. %, relative to a total weight of the composition being discussed.

As used herein, the terms "optional" or "optionally" means that the subsequently described event(s) can or cannot occur or the subsequently described component(s) may or may not be present (e.g., 0 wt. %).

The term "alkyl", as used herein, unless otherwise specified, refers to a straight, branched, or cyclic, aliphatic fragment having 1 to 26 carbon atoms, preferably 2 to 24, preferably 3 to 22, preferably 4 to 20, preferably 5 to 18, preferably 6 to 16, preferably 7 to 14, preferably 8 to 12, preferably 9 to 10. Non-limiting examples include, but are not limited to, methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, lauryl, myristyl, cetyl, stearyl, and the like, including guerbet-type alkyl groups (e.g., 2-methylpentyl, 2-ethylhexyl, 2-proylheptyl, 2-butyloctyl, 2-pentylnonyl, 2-hexyldecyl, 2-heptylundecyl, 2-octyldodecyl, 2-nonyltridecyl, 2-decyltetradecyl, and 2-undecylpentadecyl), and cycloalkyl groups such as cyclopropyl, cyclobutyl, cyclopentyl, cyclohexyl, norbornyl, and adamantyl. The term "lower alkyl" is used herein to describe alkyl groups having 1 to 5 carbon atoms (e.g., methyl, ethyl, n-propyl, etc.).

As used herein, unless otherwise specified, the term "aryl" refers to an aromatic group containing only carbon in the aromatic ring(s), such as phenyl, biphenyl, naphthyl, anthracenyl, and the like. The term "heteroarene" refers to an arene compound or aryl group where at least one carbon atom is replaced with a heteroatom (e.g., nitrogen, oxygen, sulfur) and includes, but is not limited to, pyridine, pyrimidine, quinoline, isoquinoline, pyrazine, pyridazine, indole, pyrrole, oxazole, furan, benzofuran, thiophene, benzothiophene, isoxazole, pyrazole, triazole, tetrazole, indazole, purine, carbazole, imidazole, and benzimidazole.

As used herein, "alkanoyloxy" groups are alkanoyl groups that are bound to oxygen (—O—C(O)-alkyl), for example, acetyloxy, propionyloxy, butyryloxy, isobutyryloxy, pivaloyloxy, valeryloxy, hexanoyloxy, octanoyloxy, lauroyloxy, and stearoyloxy. "Alkoxycarbonyl" substituents are alkoxy groups bound to C=O (e.g. —C(O)-Oalkyl), for example methyl ester, ethyl ester, and pivaloyl ester substitution where the carbonyl functionality is bound to the rest of the compound.

As used herein, "disubstituted amino" groups refers to an amino group substituted with alkyl and/or aryl groups (e.g. dialkylamino, diarylamino, arylalkylamino). The alkyl and/or aryl groups are as defined above (and may be optionally substituted).

As used herein, "optionally substituted" means that at least one hydrogen atom is replaced with a non-hydrogen group, provided that normal valencies are maintained and that the substitution results in a stable compound. Such optional substituents may be selected from aryl, alkoxy, aryloxy, arylalkyloxy, alkanoyloxy, carboxy, alkoxycarbonyl, hydroxy, halo (e.g. chlorine, bromine, fluorine or iodine), amino (e.g. alkylamino, acylamino, arylalkylamino, alkanoylamino, either mono- or disubstituted), oxo, amido (e.g. —CONH$_2$, —CONHalkyl, —CONHaryl, —CONHarylalkyl or cases where there are two substituents on one nitrogen), thio, alkylthio, and the like.

As used herein, a "chemodosimeter" or a "chemodosimetric chemosensor" is a molecular sensor in which a specific ion-induced chemical reaction occurs which results in a new or a changed optical signal, for example a palladium ion-induced deallylation reaction.

As used herein, the term "ratiometric" means that the output is directly proportional to input, for example, the fluorescence emission intensity changes in direct proportion to the input of palladium ions.

As used herein, "bathochromic" or "bathochromic shift" refers to a change of spectral band position in the absorption, reflectance, transmittance, or emission spectrum of a molecule to a longer wavelength. Because the red color in the visible spectrum has a longer wavelength than most other colors, the effect is also commonly called a 'red shift.'

Chemosensor

The present disclosure provides a chemosensor for the sensitive and selective detection of palladium ions ($Pd^{2+}$) in a fluid sample, including those fluid samples which contain a host of different cations. The chemosensor disclosed herein is easy to manufacture, including on-scale manufacture, and is capable of acting as a chemodosimetric and ratiometric chemosensor for the detection of palladium ions and/or determination of palladium ion concentration in the fluid sample. The chemosensor is preferably based on a fluorescein-allyloxy benzene scaffold, and when contacted to palladium ions, a deallylation reaction takes place which provides it with an "on-off" type fluoroionophoric switching property specific to palladium, to enable facile detection and quantification of palladium ions, even in the presence of other cations, such as those commonly found in wastewater and biologically relevant samples. It has been found that the chemosensor of the present disclosure, upon interaction with palladium ions, produces a remarkable bathochromic shift, e.g., a 150 nm shift, which allows for extremely easy detection and/or quantification of palladium ions.

The present disclosure thus provides a chemosensor of formula I,

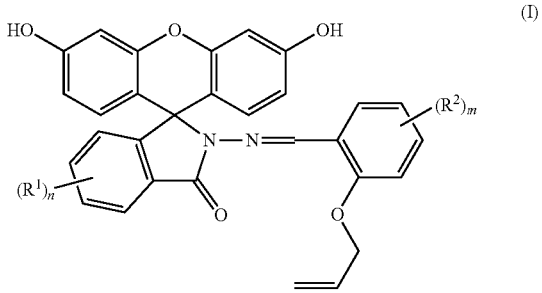

wherein:
each $R^1$ is independently an optionally substituted alkyl, an optionally substituted alkoxy, a carboxy, a disubstituted amino, an alkanoylamino, an amido, or an isothiocyano,
each $R^2$ is independently an optionally substituted alkyl, an optionally substituted aryl, an optionally substituted alkoxy, an alkanoyloxy, an optionally substituted alkoxycarbonyl, a halo, a substituted amino, a nitro, a cyano, or an azo,
n is 0 to 2, and
m is 0 to 4.

In some embodiments, when $R^1$ is present, $R^1$ may be located on the 5-position (i.e., meta to the amide group) of the isoindolin-1-one moiety and/or the 6-position (i.e., para to the amide group) of the isoindolin-1-one moiety. $R^1$ may be a $C_1$ to $C_8$ alkyl, preferably a $C_2$ to $C_7$ alkyl, preferably a $C_3$ to $C_6$ alkyl, preferably a $C_4$ to $C_5$ alkyl, the alkyl group being substituted or unsubstituted, with specific mention being made to methyl, ethyl, propyl, isopropyl, butyl, isobutyl, t-butyl, trifluoromethyl, and bromomethyl. $R^1$ may be a $C_1$ to $C_8$ alkoxy, preferably a $C_2$ to $C_7$ alkoxy, preferably a $C_3$ to $C_6$ alkoxy, preferably a $C_4$ to $C_5$ alkoxy, the alkoxy group being substituted or unsubstituted, with specific mention being made to methoxy, ethoxy, and trifluoromethoxy. $R^1$ may be a carboxy, preferably a carboxy located on the 5-position of the isoindolin-1-one moiety or the 6-position of the isoindolin-1-one moiety. $R^1$ may be a disubstituted amino group, such as a dialkylamino group, preferably a $C_1$ to $C_8$ dialkylamino, preferably a $C_2$ to $C_7$ dialkylamino, preferably a $C_3$ to $C_6$ dialkylamino, preferably a $C_4$ to $C_5$ dialkylamino, a diarylamino group, or an alkylarylamino group, preferably a $C_1$ to $C_8$ alkyl aryl amino, preferably a $C_2$ to $C_7$ alkyl aryl amino, preferably a $C_3$ to $C_6$ alkyl aryl amino, with the alkyl and/or aryl group being substituted or unsubstituted, with specific mention being made to dimethylamino, diethylamino, diisoproylamino, dipropylamino, ethylisopropylamino, methylphenylamino, and the like. $R^1$ may be an alkanoylamino, preferably a $C_1$ to $C_8$ alkanoylamino, preferably a $C_2$ to $C_7$ alkanoylamino, preferably a $C_3$ to $C_6$ alkanoylamino, preferably a $C_4$ to $C_5$ alkanoylamino, with the alkyl portion of the alkanoylamino group being substituted or unsubstituted, with specific mention being made to acetamido, iodoacetamido, propionamido, carboxamido hexanoic acid, thiopropianamido, and the like. $R^1$ may be an amido, for example, —$CONH_2$, —CONHalkyl, —CONHaryl, —CONHarylalkyl or cases where there are two alkyl and/or aryl substituents on one nitrogen, with the alkyl and/or aryl groups being substituted or unsubstituted as defined above, with specific mention being made to unsubstituted amido (—$CONH_2$), monomethylamido, and dimethylamido. $R^1$ may be a isothiocyano, preferably a isothiocyano located on the 5-position of the chemosensor (i.e., meta to the amide group of the isoindolin-1-one moiety) or the 6-position of the chemosensor (i.e., para to the amide group of the isoindolin-1-one moiety).

In some embodiments, when $R^2$ is present, $R^2$ may be located ortho, meta, and/or para to the allyloxy group. $R^2$ may be a $C_1$ to $C_8$ alkyl, preferably a $C_2$ to $C_7$ alkyl, preferably a $C_3$ to $C_6$ alkyl, preferably a $C_4$ to $C_5$ alkyl, the alkyl group being substituted or unsubstituted, with specific mention being made to methyl, ethyl, propyl, isopropyl, butyl, isobutyl, t-butyl, trifluoromethyl, and bromomethyl. $R^2$ may be an aryl, either substituted or unsubstituted, with specific mention being made to phenyl, biphenyl, naphthyl, tolyl, 2-methoxyphenyl, 4-nitrophenyl, 3-nitrophenyl, 2,3-difluorophenyl, 3,5-dimethylphenyl, 4-cyanophenyl, 4-fluorophenyl, 3-carboxyphenyl, 2,5-difluorophenyl, 3-fluorophenyl, 2,4-difluorophenyl, 2,6-difluorophenyl, 2-fluorophenyl, 4-acetylphenyl, 2,3-dichlorophenyl, 2-bromophenyl, and 2-ethylphenyl. $R^2$ may be a $C_1$ to $C_8$ alkoxy, preferably a $C_2$ to $C_7$ alkoxy, preferably a $C_3$ to $C_6$ alkoxy, preferably a $C_4$ to $C_5$ alkoxy, the alkoxy group being substituted or unsubstituted, with specific mention being made to methoxy, ethoxy, and propoxy. $R^2$ may be a alkanoyloxy (—O—C(O)-alkyl), where the alkyl group is as defined previously, with specific mention being made to acetyloxy, propionyloxy, butyryloxy, isobutyryloxy, and hexanoyloxy. $R^2$ may be a alkoxycarbonyl (e.g. —C(O)-Oalkyl), with the alkyl group is as defined previously, with specific mention being made to methyl ester, ethyl ester, and pivaloyl ester. $R^2$ may be a halo, preferably chlorine, bromine, or fluorine. $R^2$ may be a substituted amino group, either monosubstituted or disubstituted with an alkyl and/or aryl group, which may be substituted or unsubstituted, such as a $C_1$ to $C_8$ monoalkyl or dialkylamino, preferably a $C_2$ to $C_7$ monoalkyl or dialkylamino, preferably a $C_3$ to $C_6$ monoalkyl or dialkylamino, preferably a $C_4$ to $C_5$ monoalkyl or dialkylamino, a monoaryl or diarylamino group, or an alkylarylamino group, preferably a $C_1$ to $C_8$ alkyl aryl amino, preferably a $C_2$ to $C_7$ alkyl aryl amino, preferably a $C_3$ to $C_6$ alkyl aryl amino, with specific mention being made to ethylamino, methoxyethylamino, dimethylamino, diethylamino, diisoproylamino, dipropylamino, ethylisopropylamino, methylphenylamino, and the like. $R^2$ may also be a nitro, a cyano, or an azo.

In some embodiments, n is 0 to 2, preferably 0 to 1, preferably 0. In some embodiments, m is 0 to 4, preferably 0 to 3, preferably 0 to 2, preferably 0 to 1, preferably 0. In some embodiments, n +m is equal to 0 to 2, preferably 0 to 1.

In some embodiments, n is 0 or 1, and when n is 1, $R^1$ is preferably an optionally substituted alkyl or an optionally substituted alkoxy. In some embodiments, m is 0 or 1, and when m is 1, $R^2$ is preferably an optionally substituted alkyl, an optionally substituted alkoxy, ora halo.

In preferred embodiments, both n and m are 0, and the chemosensor is

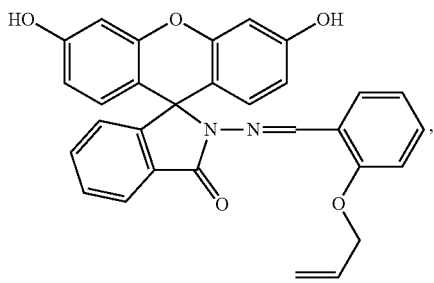

also referred to herein as "compound 1".

One acceptable example for making the chemosensor of formula I will now be described. Fluorescein (3',6'-dihydroxyspiro[isobenzofuran-1(3H),9'-[9H]xanthen]-3-one) or a suitable fluorescein derivative may first be reacted with hydrazine ($NH_2NH_2$) in a suitable solvent, for example a polar protic solvent such as methanol, ethanol, propanol, isopropanol, etc., to form a fluorescein hydrazide of formula II,

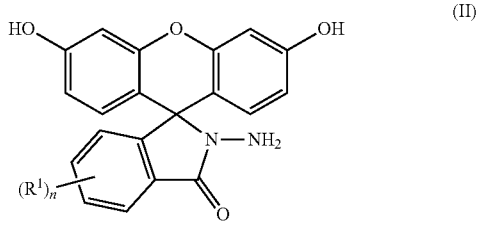

wherein $R^1$ and n are as defined above.

Fluorescein derivatives may be commercially available or otherwise known to those of ordinary skill in the art (see e.g., U.S. Pat. Nos. 5,352,803A, 8,084,627B2), for example, those fluorescein derivatives prepared from Friedel-Crafts reaction of a substituted phthalic anhydride with resorcinol under Lewis acid activation or modified variants thereof. Suitable examples of fluorescein derivatives that may be used as a starting material herein include, but are not limited to, fluorescein 5-isothiocyanate, fluorescein 6-isothiocyanate, 5-carboxyfluorescein, 6-carboxyfluorescein, 5-(bromomethyl)fluorescein, 5-(iodoacetamido)fluorescein, 5-(acetamido)fluorescein, 5-dimethylaminofluoroscein, 6-[fluorescein-5-carboxamido]hexanoic acid, 6-[fluorescein-6-carboxamido]hexanoic acid, 5-methylfluorescein, 6-methylfluorescein, 5-bromomethylfluorescein, 5-hydroxymethyl fluorescein, and 6-hydroxymethyl fluorescein. The fluorescein or the fluorescein derivative may be reacted with hydrazine at 25 to 100° C., preferably 50 to 90° C., preferably 60 to 80° C., preferably 65 to 70° C., or under conditions of reflux for a particular solvent.

In preferred embodiments, fluorescein is used as starting material to form the fluorescein hydrazide of formula II wherein n is 0.

Separately, salicylaldehyde (2-hydroxybenzaldehyde) or a substituted salicylaldehyde derivative may be subjected to O-allylation using an allyl halide (e.g., allyl bromide, allyl chloride, allyl iodide) or other allylic electrophile (e.g., allyl trifluoromethanesulfonate) in the presence of a base, to form the allyloxy compound of formula III,

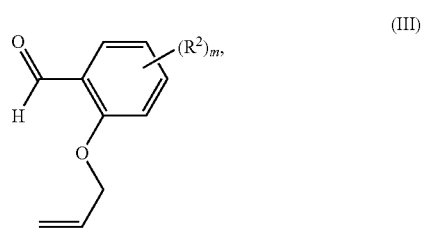

wherein $R^2$ and m are as defined previously. The O-allylation reaction may be performed, for example, in a polar aprotic solvent such as acetonitrile, tetrahydrofuran, dichloromethane, N-methylpyrrolidone, dimethylformamide, dimethylsulfoxide, propylene carbonate, and may be performed at a temperature of 25 to 150° C., preferably 45 to 125° C., preferably 55 to 100° C., preferably 65 to 90° C., preferably 75 to 85° C. Exemplary bases that may be employed for the O-allylation reaction include, but are not limited to, a carbonate base (e.g., $K_2CO_3$, $Na_2CO_3$, $Li_2CO_3$, $Cs_2CO_3$), an alkoxide base (e.g., LiOtBu, NaOtBu, KOtBu), an acetate base (e.g., LiOAc, NaOAc, KOAc), a fluoride base (e.g., KF, CsF), and an organic base (e.g., DBU).

Suitable substituted salicylaldehyde derivatives which may be O-allylated, include, but are not limited to, 5-tert-butyl-2-hydroxy-3-iodobenzaldehyde, 5-tert-butyl-3-bromo-2-hydroxybenzaldehyde, 5-tert-butyl-3-(3-bromopropyl)-2-hydroxybenzaldehyde, 6-phenylsalicylaldehyde, 5-bromosalicylaldehyde, 5-chlorosalicylaldehyde, 3,5-bromosalicylaldehyde, 3,5-diiodosalicylaldehyde, 3,5-dibromosalicylaldehyde, 5-iodosalycylaldehyde, 3,5-dichlorosalicylaldehyde, 4-(diethylamino)salicylaldehyde, methyl 3-formyl-4-hydroxybenzoate, 2-hydroxy-5-(trifluoromethoxy)benzaldehyde, 3-tert-butyl-2-hydroxybenzaldehyde, 3,5-di-tert-butyl-2-hydroxybenzaldehyde, 2-hydroxy-5-methoxybenzaldehyde, 2-hydroxy-4-methoxybenzaldehyde, 3-ethoxysalicylaldehyde, 2-hydroxy-5-nitrobenzaldehyde, 2-hydroxy-3-nitrobenzaldehy de, as well as those salicylaldehyde derivatives described in US10040800B2 and U.S. Pat. No. 5,185,027A—each incorporated herein by reference in its entirety.

In preferred embodiments, salicylaldehyde is used as starting material to form the allyloxy compound of formula III wherein m is 0.

Then, the fluorescein hydrazide of formula II may be reacted with the allyloxy compound of formula III under condensation conditions to form the chemosensor of formula I. The condensation reaction may be performed using a polar protic reaction solvent such as methanol, ethanol, propanol, isopropanol, nitromethane, preferably ethanol, and at a temperature of 25 to 100° C., preferably 50 to 90° C., preferably 60 to 80° C., preferably 65 to 70° C., or under conditions of reflux for a particular solvent.

It has been found that the resulting chemosensor is extremely sensitive for the detection of palladium ions ($Pd^{2+}$) in various fluids, and is advantageously selective towards palladium ions even when other metal cations are present in abundance. Without being bound by theory, it is believed that the allyloxy group of the chemosensor of formula I inhibits the excited state intramolecular proton transfer (ESIPT) from the allyloxy benzene moiety to the fluorescein-based ring system, and thus the chemosensor of formula I only exhibits a xanthene type absorption peak and a blue fluorescence emissions peak (switched off). However, upon deallylation to form a deallylated chemosensor of formula IV below, a dramatic redshift in absorption and/or fluorescence emission occurs due to the restoration of the excited state intramolecular proton transfer (ESIPT) phenomenon between the now phenol- or phenoxy-moeity and the fluorescein-based ring system (switched on),

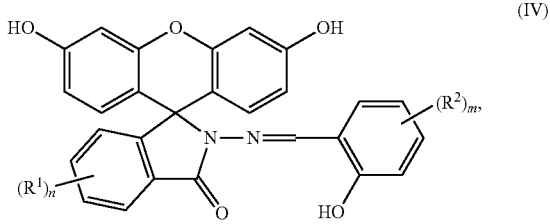

(IV)

wherein $R^1R^2$, n, and m are as defined previously.

In terms of absorption, said deallylation reaction provides a bathochromic (red) shift of 13 to 27 nm, preferably 15 to 26 nm, preferably 17 to 25 nm, preferably 19 to 24 nm, preferably 20 to 22 nm. In terms of fluorescence emission, said deallylation reaction provides a bathochromic (red) shift of 130 to 170 nm, preferably 135 to 165 nm, preferably 140 to 160 nm, preferably 145 to 155 nm, preferably 150 nm. Due to the size of shift in the spectral bands, in particular the fluorescence emission peaks, between the chemosensor of formula I and the deallylated chemosensor of formula IV, the identification of palladium is facile, and minute quantities of palladium can be detected without interference.

Further, due to the allylophilic nature of palladium ions ($Pd^{2+}$), it has been found that the chemosensor of formula I is sensitive only to the presence of palladium ions (ratiometric response), whereas other metal cations such as cations of sodium, potassium, calcium, magnesium, barium, strontium, rubidium, cesium, iron, cobalt, copper, nickel, zinc, cadmium, mercury, silver, aluminum, gallium, and lead do not cause substantial deallylation to occur, even when present at 100-fold higher concentrations than palladium. Thus, the chemosensor of formula I may be categorized as a chemodosimetric chemosensor, whereby a specific ion ($Pd^{2+}$) induces a deallylation reaction resulting in a change in optical signal that can be easily identified and may be used for detecting palladium and/or determining palladium ion concentration. In some embodiments, the chemosensor of formula I has a palladium ion ($Pd^{2+}$) fluorescence quantum yield of 0.2 to 0.3, preferably 0.21 to 0.29, preferably 0.22 to 0.28, preferably 0.23 to 0.27, preferably 0.24 to 0.26, preferably 0.25.

The chemosensor of formula I, owing in part to its chemodosimetric deallylation-based sensing mechanism, stands in stark contrast to many fluorescein derived Schiff base chemosensors, which rely on metal binding/coordination/chelation between multiple heteroatoms to produce an optical effect, see for example, US2018/0194944A1; CN10845651(A); Das, B. et al. "Fluorescein derived Schiff base as fluorimetric zinc (II) sensor via 'turn on' response and its application in live cell imaging" Spectrochimica Acta Part A: Molecular and Biomolecular Spectroscopy, 2019, 212, 222-231; Zhang, Li et al. "A selectively fluorescein-based colorimetric probe for detecting copper(II) ion" Spectrochimica Acta Part A: Molecular and Biomolecular Spectroscopy, 2014, 133, 54-59, each incorporated herein by reference in its entirety.

A Method of Detecting Palladium Ions

The present disclosure also provides a method of detecting palladium ions in a fluid sample that involves contacting the fluid sample with a solution of the chemosensor of formula I to form a mixture, and measuring at least one of an UV-Vis absorption profile and a fluorescence emission profile of the mixture to determine whether palladium is present in the fluid sample and/or to quantify the amount of palladium present in the fluid sample, based on the bathochromic spectral changes discussed above.

Fluid Sample

The fluid sample that may be analyzed by the methods of the present disclosure is not particularly limited, and may be aqueous, an oil-in-water mixture, or a mixed aqueous and organic solvent mixture. The fluid sample may be obtained from any source that may contain or is suspected of containing palladium ions. In some embodiments, the fluid sample is obtained from a natural water source (lakes, rivers, oceans, aquifers, etc.). In some embodiments, the fluid sample is a wastewater, particularly an industrial wastewater, for example, wastewater produced during pharmaceutical manufacturing operations, automotive manufacturing processes such as from fuel cell production facilities, alloying industries, etc. In some embodiments, the fluid sample is a bodily fluid, for example a bodily fluid such as saliva, sweat, blood, or urine obtained from a person exposed to or suspected to have been exposed to palladium.

In some embodiments, the fluid sample is aqueous, and is substantially free of both oil and organic solvent. The aqueous fluid may be fresh water (e.g., water obtained from streams, rivers, lakes, ground water, aquifers, purified water, tap water, wastewater having low salinity such as pharmaceutical wastewater deposited into fresh water sources, etc.) or salt water (e.g., seawater, coastal aquifers, or wastewater having high salinity).

In some embodiments, the fluid sample is an oil-in-water mixture, and may contain up to 10%, preferably up to 8%, preferably up to 6%, preferably up to 4%, preferably up to 2%, preferably up to 1% by volume of an oil based on a total volume of the fluid sample. The oil may include a natural oil, a synthetic oil, or both. Examples of oils from natural sources include, but are not limited to, kerosene, diesel oils, crude oils, gas oils, fuel oils, paraffin oils, mineral oils, low toxicity mineral oils, other petroleum distillates, and any combination thereof. Examples of synthetic oils include, but are not limited to, polyolefins, polydiorganosiloxanes, siloxanes, organosiloxanes, as well as mixtures thereof.

In some embodiments, the fluid sample is a mixed aqueous and organic solvent mixture. The organic solvent that may be optionally present in the fluid sample is not particularly limited, and may include organic solvent(s) employed during various industrial processes that produce a wastewater that may contain or is suspected of containing palladium ions, for example, pharmaceutical manufacturing operations, automotive manufacturing processes such as fuel cell production facilities, alloying industries, etc. The organic solvent may be miscible or immiscible with water. Exemplary organic solvents that may be present in the fluid sample include, but is not limited to, aromatic solvents (e.g., benzene, ethylbenzene, o-xylene, m-xylene, p-xylene, and mixtures of xylenes, toluene, mesitylene, anisole, 1,2-dimethoxybenzene, α,α,α,-trifluoromethylbenzene, fluorobenzene, heavy aromatic naptha), alkane solvents (e.g., pentane, cyclopentane, hexanes, cyclohexane, heptanes, cycloheptane, octanes), ethers (e.g. diethyl ether, tetrahydrofuran, 1,4-dioxane, tetrahydropyran, t-butyl methyl ether, cyclopentyl methyl ether, di-isopropyl ether), glycol ethers (e.g. 1,2-dimethoxyethane, diglyme, triglyme), chlorinated solvents (e.g. chlorobenzene, dichloromethane, 1,2-dichloroethane, 1,1-dichloroethane, chloroform, carbon tetrachloride), ester solvents (e.g. ethyl acetate, propyl acetate), ketones (e.g. acetone, butanone), formamides/acetamides (e.g., formamide, dimethyl formamide, dimethyl acetamide), monoalcohols (e.g., methanol, ethanol, propanol, isopropanol, n-butanol, isobutanol, n-pentanol, n-hexanol, terpineol, menthol, prenol, 3-methyl-3-buten-1-ol, 2-ethyl-1-hexanol, 2-ethyl-1-butanol, 2-propylheptan-1-ol, 2-butyl-1-octanol, benzyl alcohol), polyalcohols including glycols (e.g., ethylene glycol, diethylene glycol, triethylene glycol, tetraethylene glycol, propylene glycol, dipropylene glycol, 1,3-propanediol, 1,3-butanediol, 1,4-butanediol, 1,6-hexanediol, glycerol, pentaerythritol, manitol, sorbitol), as well as mixtures thereof. The fluid sample may contain up to 30%, preferably up to 25%, preferably up to 20%, preferably up to 15%, preferably up to 10%, preferably up to 5%, preferably up to 2%, preferably up to 1% by volume of an organic solvent(s) based on a total volume of the fluid sample.

In addition to optionally containing an oil(s) and/or an organic solvent(s) as described above, the fluid sample may optionally contain suspended solids. In some embodiments, the fluid sample contains greater than 55% v/v of water, preferably greater than 60% v/v of water, preferably greater than 65% v/v of water, preferably greater than 70% v/v of water, preferably greater than 75% v/v of water, preferably greater than 80% v/v of water, preferably greater than 85% v/v of water, preferably greater than 90% v/v of water, preferably greater than 95% v/v of water, preferably greater than 99% v/v of water, based on a total volume of the fluid sample.

The fluid sample may contain palladium ions ($Pd^{2+}$). When present, the palladium ions may be present in the fluid sample at a concentration of 0.05 to 4,000 ppm, preferably 0.1 to 3,500 ppm, preferably 0.5 to 3,000 ppm, preferably 1 to 2,500 ppm, preferably 5 to 2,000 ppm, preferably 10 to 1,500 ppm, preferably 20 to 1,000 ppm, preferably 40 to 900 ppm, preferably 60 to 800 ppm, preferably 80 to 700 ppm, preferably 100 to 600 ppm, preferably 120 to 500 ppm, preferably 140 to 400 ppm, preferably 160 to 300 ppm, preferably 180 to 250 ppm, preferably 200 to 220 ppm. Examples of palladium species that may be present in the fluid sample, which are in the form of palladium ions or are capable of forming palladium ions in situ include, but are not limited to, palladium(II) chloride ($PdCl_2$), palladium tetrakis ($Pd(PPh_3)_4$), palladium(II) acetate ($Pd(OAc)_2$), bis(triphenylphosphine)palladium(II) dichloride ($PdCl_2(PPh_3)_2$), tris(dibenzylideneacetone)dipalladium ($Pd_2(dba)_3$), bis(dibenzylideneacetone)palladium(0) ($Pd(dba)_2$), palladium(II) oxide (PdO), palladium(II) oxide (PdS), palladium(II) acetylacetonate ($Pd(acac)_2$), bis(tri-tert-butylphosphine)palladium(0) ($Pd(PtBu_3)_2$), bis(benzonitrile)palladium(II) chloride (($C_6H_5CN)_2PdCl_2$), palladium(II) nitrate ($Pd(NO_3)_2$), palladium(II) trifluoroacetate ($Pd(TFA)_2$), tetrakis(acetonitrile)palladium(II) tetrafluoroborate ($Pd(CH_3CN)_4(BF_4)_2$), (ethylenediamine)palladium(II) chloride ($Pd(H_2NCH_2CH_2NH_2)Cl_2$), palladium(II) hexafluoroacetylacetonate ($Pd(C_5HF_6O_2)_2$), bis(triphenylphosphine)palladium(II) diacetate ($[(C_6H_5)_3P]_2Pd(CH_3COO)_2$), palladium(II) bromide ($PdBr_2$), palladium(II)[1,3-bis(diphenylphosphino)propane]-bis(benzonitrile)-bis-tetrafluoroborate ($[Pd(dppp)(PhCN)_2](BF_4)_2$), palladium(II) sulfate ($PdSO_4$), palladium (II) cyanide ($Pd(CN)_2$), and palladium(II) propionate (($C_2H_5CO_2)_2Pd$), just to name a few.

The fluid sample may also optionally include one or more (non-palladium) cations, including heavy and transitional metal cations as well as alkali and alkaline earth metal cations, such as cations of sodium, potassium, calcium, magnesium, barium, strontium, rubidium, cesium, iron (ferrous and ferric), cobalt, copper, manganese, nickel, zinc, cadmium, mercury, silver, aluminum, gallium, chromium and lead, including mixtures thereof. Representative examples of anions which may also be present in the fluid sample include, but are not limited to, chloride, carbonate, bicarbonate, sulfate, bromide, iodide, acetate, hydroxide, sulfide, hydrosulfide, chlorate, fluoride, hypochlorite, nitrate, nitrite, perchlorate, peroxide, phosphate, phosphite, sulfite, hydrogen phosphate, hydrogen sulfate, as well as mixtures thereof.

In some embodiments, sodium ions may be present in the fluid sample in amounts of at least 50 ppm, and up to 50,000 ppm, preferably up to 40,000 ppm, preferably up to 30,000 ppm, preferably up to 20,000 ppm, preferably up to 10,000 ppm, preferably up to 5,000 ppm, preferably up to 1,000 ppm, preferably up to 500 ppm, preferably up to 200 ppm.

In some embodiments, potassium ions may be present in the fluid sample in amounts of at least 5 ppm, and up to 20,000 ppm, preferably up to 15,000 ppm, preferably up to 10,000 ppm, preferably up to 5,000 ppm, preferably up to 1,000 ppm, preferably up to 500 ppm, preferably up to 100 ppm.

The fluid sample may also generally contain up to 50,000 ppm of multivalent (non-palladium) cations (e.g., magnesium ions, calcium ions, iron ions, strontium ions, barium ions, lead ions, copper ions, cobalt ions, manganese ions, nickel ions, zinc ions, and/or aluminum ions, etc.), for example at least 50 ppm, preferably at least 75 ppm, preferably at least 100 ppm, preferably at least 150 ppm, preferably at least 200 ppm, preferably at least 500 ppm, preferably at least 1,000 ppm, preferably at least 2,000 ppm, preferably at least 5,000 ppm, and up to 50,000 ppm, preferably up to 40,000 ppm, preferably up to 30,000 ppm, preferably up to 20,000 ppm, preferably up to 10,000 ppm, preferably up to 7,000 ppm, preferably up to 6,000 ppm total of multivalent cations. For example, barium and/or strontium ions may be present in the fluid sample in amounts of at least 100 ppm, preferably at least 200 ppm, preferably at least 400 ppm, preferably at least 600 ppm, preferably at least 800 ppm, preferably at least 1,000 ppm, preferably at least 1,200 ppm, preferably at least 1,400 ppm, preferably at least 1,600 ppm, preferably at least 1,800 ppm, preferably at least 2,000 ppm, preferably at least 2,500 ppm, preferably at least 3,000 ppm, preferably at least 4,000 ppm, and up to 10,000 ppm, preferably up to 9,000 ppm, preferably up to 8,000 ppm, preferably up to 7,000 ppm, preferably up to 6,000 ppm, preferably up to 5,000 ppm, preferably up to 4,800 ppm, preferably up to 4,600 ppm. Magnesium ions, for example in amounts up to 2,500 ppm, preferably up to 2,000 ppm, preferably up to 1,500 ppm, preferably up to 1,000 ppm, preferably up to 500 ppm, preferably up to 100 ppm, and/or calcium ions, for example in amounts up to 15,000 ppm, preferably up to 12,000 ppm, preferably up to 10,000 ppm, preferably up to 8,000 ppm, preferably up to 6,000 ppm, preferably up to 4,000 ppm, preferably up to 2,000 ppm, preferably up to 1,000 ppm, preferably up to 500 ppm, may also be present in the fluid sample.

In some embodiments, the fluid sample has a total dissolved solids (TDS) content of up to 200,000 mg/L, for example 100 to 200,000 mg/L, preferably 500 to 180,000 mg/L, preferably 1,000 to 150,000 mg/L, preferably 1,500 to 100,000 mg/L, preferably 2,000 to 80,000 mg/L, preferably 3,000 to 60,000 mg/L, preferably 4,000 to 40,000 mg/L, preferably 5,000 to 20,000 mg/L, preferably 6,000 to 10,000 mg/L.

Solution

The solution of the present disclosure preferably contains the chemosensor of formula I and water. In general, the chemosensor of formula I may be present in the solution in an amount of 0.2 to 20 µM, preferably 0.5 to 15 µM, preferably 1 to 10 µM, preferably 2 to 9 µM, preferably 3 to 8 µM, preferably 4 to 7 µM, preferably 5 to 6 µM, based on a total volume of the solution, although concentrations above or below these values may be employed depending on various factors, such as the suspected amount of palladium ions present in the fluid sample, whether the solution will be titrated, etc. Preferably, the chemosensor of formula I is the only palladium-specific chemosensor present in the solution. Preferably, the chemosensor of formula I is the only chemosensor present in the solution.

In some embodiments, the solution optionally includes an organic solvent, for example to aid solvation of organic matter or other insoluble that may be present in the fluid sample as well as certain derivatives of the chemosensor of formula I. Preferably, when present, an organic solvent is selected that is miscible in water and does not interfere with the optical signal/measurement/read-out of the methods described herein. Specific examples of acceptable organic solvents include, but are not limited to, ethers (e.g. diethyl ether, tetrahydrofuran, 1,4-dioxane, tetrahydropyran, t-butyl methyl ether, cyclopentyl methyl ether, di-isopropyl ether), glycol ethers (e.g. 1,2-dimethoxyethane, diglyme, triglyme), ketones (e.g. acetone, butanone), formamides/acetamides (e.g., formamide, dimethyl formamide, dimethyl acetamide), monoalcohols (e.g., methanol, ethanol, propanol, isopropanol, n-butanol, isobutanol, n-pentanol, n-hexanol, terpineol, menthol, prenol, 3-methyl-3-buten-1-ol, 2-ethyl-1-hexanol, 2-ethyl-1-butanol, 2-propylheptan-1-ol, 2-butyl-1-octanol, benzyl alcohol), polyalcohols including glycols (e.g., ethylene glycol, diethylene glycol, triethylene glycol, tetraethylene glycol, propylene glycol, dipropylene glycol, 1,3-propanediol, 1,3-butanediol, 1,4-butanediol, 1,6-hexanediol, glycerol, pentaerythritol, manitol, sorbitol), as well as mixtures thereof. In preferred embodiments, the organic solvent is dimethylformamide (DMF). A ratio of water to the organic solvent in the solution may vary widely depending on, for example, the type of fluid sample, the type and solubility properties of the materials contained therein, etc. Typically, when an organic solvent is present, a ratio of water to the organic solvent ranges from 5:1 to 20:1, preferably 6:1 to 18:1, preferably 7:1 to 16:1, preferably 8:1 to 14:1, preferably 9:1 to 12:1.

Another advantage of the chemosensor of formula I is its ability to operate in a broad pH range, for example, at a pH of from 5 to 9, preferably 5.5 to 8.5, preferably 6 to 8, preferably 6.5 to 7.5, preferably 7, which make it suitable for testing in various physiological and environmental applications. Therefore, the use of buffers are not always needed. However, in some embodiments, the solution may further include a buffer to ensure the resulting mixture has a suitable pH range. Therefore, in some embodiments, a buffer may be optionally included in the solution, for example, in a concentration of 1 to 50 mM, preferably 2 to 45 mM, preferably 3 to 40 mM, preferably 4 to 35 mM, preferably 5 to 30 mM, preferably 6 to 25 mM, preferably 7 to 20 mM, preferably 8 to 15 mM, preferably 9 to 12 mM, preferably 10 to 11 mM, based on a total volume of the solution.

The buffer may be a phosphate buffer. a borate buffer, a citrate buffer. an acetate buffer, a sulfonic acid buffer (in particular a zwitterionic sulfonic acid buffer), an amino alcohol-based buffer, an arsenate buffer, as well as mixtures thereof. Specific examples of buffers that may be utilized herein include, but are not limited to, monosodium phosphate, monopotassium phosphate, disodium phosphate, citric acid, acetic acid, borate, N-cyclohexyl-2-aminoethanesulfonic acid (CHES), tris(hydroxymethyl)methylamino] propanesulfonic acid (TAPS), 2-(bis(2-hydroxyethyl)amino) acetic acid (bicine), tris(hydroxymethyl)aminomethane) (tris), 3-[N-tris(hydroxymethyl)methylamino]-2-hydroxypropanesulfonic acid (tricine), 3-[N-tris(hydroxymethyl) methylamino]-2-hydroxypropanesulfonic acid (TAPSO), 4-(2-hydroxyethyl)-1-piperazineethanesulfonic acid (HEPES), 2-[[1,3-dihydroxy-2-(hydroxymethyl)propan-2-yl]amino]ethanesulfonic acid (TES), piperazine-N,N'-bis(2-ethanesulfonic acid) (MOPS), piperazine-N,N'-bis(2-ethanesulfonic acid) (PIPES), dimethylarsenic acid (cacodylate), 2-(N-morpholino)ethanesulfonic acid (MES), bis-tris methane, N-(2-acetamido)iminodiacetic acid (ADA), N-(2-acetamido)-2-aminoethanesulfonic acid (ACES), 3-morpholino-2-hydroxypropanesulfonic acid (MOPSO), cholamine chloride hydrochloride, triethanolamine, 3-[4-(2-hydroxyethyl)piperazin-1-yl]propane-1-sulfonic acid (HEPPS), N-(2-hydroxyethyl)piperazine-N'-(4-butanesulfonic acid (HEPBS), aminomethyl propanol (AMP), including mixtures thereof. In preferred embodiments, the buffer is 4-(2-hydroxyethyl)-1-piperazineethanesulfonic acid (HEPES).

The solution may also optionally include a surfactant, for example, when the fluid sample to be tested is an oil-in-water mixture, for example, when testing various wastewaters. The surfactant may be a cationic, anionic, non-ionic, and/or amphoteric surfactant, and may be present in the solution in an amount of up to 5 wt. %, preferably up to 4 wt. %, preferably up to 3 wt. %, preferably up to 2 wt. %, preferably up to 1 wt. %, preferably up to 0.5 wt. %, preferably up to 0.1 wt. %, based on a total weight of the solution.

Cationic surfactants may include, but are not limited to
- a protonated amine formed from a reaction between a $C_6$-$C_{26}$ alkyl amine compound and an acid (e.g., acetic acid, formic acid, propionic acid, butyric acid, pentanoic acid, hexanoic acid, oxalic acid, malonic acid, lactic acid, glyceric acid, glycolic acid, malic acid, citric acid, benzoic acid, p-toluenesulfonic acid, trifluoromethanesulfonic acid, hydrochloric acid, nitric acid, phosphoric acid, sulfuric acid, hydrobromic acid, perchloric acid, hydroiodic acid, etc.), such as protonated salts of $C_6$-$C_{26}$ alkyl monoamines, $C_6$-$C_{26}$ alkyl (poly)alkylene polyamines, and alkoxylated fatty amines;
- a protonated $C_6$-$C_{26}$ alkyl amidoamine formed from a reaction between a $C_6$-$C_{26}$ alkyl amidoamine compound and an acid (for example the acids listed above), such as protonated forms of the amide reaction product between any fatty acid previously listed (or ester derivative thereof) with a polyamine (e.g., putrescine, cadaverine, ethylene diamine, $N^1,N^1$-dimethylethane-1,2-diamine, $N^1,N^1$-dimethylpropan-1,3-diamine, $N^1,N^1$-diethylethane-1,2-diamine, $N^1,N^1$-diethylpropane-1,3-diamine, speiiiiidine, 1,1,1-tris(aminomethyl) ethane, tris(2-aminoethyl)amme, spermine, TEPA, DETA, TETA, AEEA, PEHA, HEHA, dipropylene triamine, tripropylene tetramine, tetrapropylene pentamine, pentapropylene hexamine, hexapropylene heptamine, dibutylene triamine, tributylene tetramine, tetrabutylene pentamine, pentabutylene hexamine, hexabutylene heptamine), with specific mention being made to protonated forms of stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylmine, behenamidoethyldiethylamine, behenamidoethyldimethylamine, arachidamidopropyldimethylamine, arachidamidopropyldiethylamine, arachidamidoethyldiethylamine, and arachidamidoethyldimethylamine; and a quaternary ammonium compound made from alkylation with suitable alkylating agents (e.g., dimethyl sulfate, methyl chloride or bromide, benzyl chloride or bromide, $C_6$-$C_{26}$ alkyl chloride or bromide, etc.) of a tertiary $C_6$-$C_{26}$ alkyl amine, an alkoxylated (tertiary) amine, or an aprotic nitrogenous heteroarene (optionally substituted) having at least one aromatic nitrogen atom with a reactive lone pair of electrons, with specific mention being made to a tri-fatty alkyl lower alkyl ammonium compound (e.g., trioctyl methyl ammonium chloride), a $C_{10}$-$C_{18}$ alkyl trimethyl ammonium chloride or methosulfate, a di-$C_{10}$-$C_{18}$ alkyl dimethyl ammonium chloride or methosulfate, a $C_{10}$-$C_{18}$ alkyl benzyl dimethyl ammonium chloride, a methyl quaternized $C_6$-$C_{22}$ alkyl propylene diamine, a methyl quaternized $C_6$-$C_{22}$ alkyl propylene triamine, a methyl quaternized $C_6$-$C_{22}$ alkyl propylene tetraamine, a N-$C_{10}$-$C_{18}$ alkyl pyridinium or a quinolinium bromide or chloride such as N-octyl pyridinium bromide, N-nonyl pyridinium bromide, N-decyl pyridinium bromide, N-dodecyl pyridinium bromide, N-tetradecyl pyridinium bromide, N-dodecyl pyridinium chloride, N-cyclohexyl pyridinium bromide, naphthyl methyl quinolinium chloride, naphthyl methyl pyridinium chloride, and cetylpyridinium chloride (for example those disclosed in CN101544903B—incorporated herein by reference in its entirety);

as well as mixtures thereof.

Anionic surfactants may include, but are not limited to:
sulfates, such as alkyl sulfates, alkyl-ester-sulfates, alkyl ether sulfates, alkyl-alkoxy-ester-sulfate, sulfated alkanolamides, glyceride sulfates, in particular, sulfates of fatty alcohols or polyoxyalkylene ethers of fatty alcohols such as sodium dodecyl sulfate, sodium laureth sulfate, ammonium lauryl sulfate, potassium lauryl sulfate, sodium myreth sulfate;

sulfonates such as alkyl sulfonates, fatty alkyl-benzene sulfonates, lower alkyl-benzene sulfonates, alpha olefin sulfonates, lignosulfonates, sulfo-carboxylic compounds, for example, dodecyl benzene sulfonate, dioctyl sodium sulfosuccinate, perfluorooctanesulfonate (PFOS), perfluorobutanesulfonate;

phosphates such as alkyl aryl ether phosphates, alkyl ether phosphates, phosphates of fatty alcohols or polyoxyalkylene ethers of fatty alcohols such as cetyl phosphate salts, dicetyl phosphate salts, ceteth-10-phosphate salts;

carboxylate salts of fatty acids, acylamino acids, lactylates, and/or fatty alcohols/polyoxyalkylene ethers of fatty alcohols such as sodium stearate, vegetable oil-based anionic surfactants (e.g., palm oil anionic surfactant), sodium behenoyl lactylate, sodium isostearoyl lactylate, sodium caproyl lactylate, sodium laureth-5 carboxylate, sodium laureth-6 carboxylate, sodium laureth-11 carboxylate;

and mixtures thereof.

Non-ionic surfactants may include, but are not limited to:
amides or alkanolamides of fatty acids, that is, amide reaction products between a fatty acid and an amine or alkanolamine compound, such as coconut fatty acid monoethanolamide (e.g., N-methyl coco fatty ethanol amide), coconut fatty acid diethanolamide, oleic acid diethanolamide, palm based oleylamine, and vegetable oil fatty acid diethanolamide;

alkoxylated alkanolamides of fatty acids, preferably ethoxylated and/or propoxylated variants of the alkanolamides of fatty acids using for example anywhere from 2 to 30 EO and/or PO molar equivalents, preferably 3 to 15 EO and/or PO molar equivalents, preferably 4 to 10 EO and/or PO molar equivalents, preferably 5 to 8 EO and/or PO molar equivalents per moles of the alkanolamide of the fatty acid (e.g., coconut fatty acid monoethanolamide with 4 moles of ethylene oxide);

amine oxides, such as N-cocoamidopropyl dimethyl amine oxide and dimethyl $C_6$-$C_{22}$ alkyl amine oxide (e.g., dimethyl coco amine oxide);

fatty esters, such as ethoxylated and/or propoxylated fatty acids (e.g., castor oil with 2 to 40 moles of ethylene oxide), alkoxylated glycerides (e.g., PEG-24 glyceryl monostearate), glycol esters and derivatives, monoglycerides, polyglyceryl esters, esters of polyalcohols, and sorbitan/sorbitol esters;

ethers, such as (i) alkoxylated $C_1$-$C_{22}$ alkanols, which may include alkoxylated $C_1$-$C_5$ alkanols, preferably ethoxylated or propoxylated $C_1$-$C_5$ alkanols (e.g., dipropylene glycol n-butyl ether, tripropylene glycol n-butyl ether, dipropylene glycol methyl ether, tripropylene glycol methyl ether, diethylene glycol n-butyl ether, triethylene glycol n-butyl ether, diethylene glycol methyl ether, triethylene glycol methyl ether) and alkoxylated $C_6$-$C_{26}$ alkanols (including alkoxylated fatty alcohols), preferably alkoxylated $C_7$-$C_{22}$ alkanols, more preferably alkoxylated $C_8$-$C_{14}$ alkanols, preferably ethoxylated or propoxylated (e.g., cetyl stearyl alcohol with 2 to 40 moles of ethylene oxide, lauric alcohol with 2 to 40 moles of ethylene oxide, oleic alcohol with 2 to 40 moles of ethylene oxide, ethoxylated lanoline derivatives, laureth-3, ceteareth-6, ceteareth-11, ceteareth-15, ceteareth-16, ceteareth-17, ceteareth-18, ceteareth-20, ceteareth-23, ceteareth-25, ceteareth-27, ceteareth-28, ceteareth-30, isoceteth-20, laureth-9/myreth-9, and PPG-3 caprylyl ether); (ii) alkoxylated polysiloxanes; (iii) ethylene oxide/propylene oxide copolymers (e.g., PPG-1-PEG-9-lauryl glycol ether, PPG-12-buteth-16, PPG-3-buteth-5, PPG-5-buteth-7, PPG-7-buteth-10, PPG-9-buteth-12, PPG-12-buteth-16, PPG-15-buteth-20, PPG-20-buteth-30, PPG-28-buteth-35, and PPG-33-buteth-45); and (iv) alkoxylated alkylphenols;

alkyl polyglycosides (APGs) such as those made from reaction between fatty alcohols and glucose;

and mixtures thereof.

Amphoteric surfactants may include, but are not limited to:
$C_6$-$C_{22}$ alkyl dialkyl betaines, such as fatty dimethyl betaines (R—N(CH$_3$)$_2$(+)—CH$_2$COO$^-$), obtained from a $C_6$-$C_{22}$ alkyl dimethyl amine which is reacted with a monohaloacetate salt (e.g., sodium monochloroacetate), such as $C_{12}$-$C_{14}$ dimethyl betaine (carboxylate methyl $C_{12}$-$C_{14}$ alkyl dimethylammonium);

$C_6$-$C_{22}$ alkyl amido betaines (R—CO—NH—CH$_2$CH$_2$CH$_2$—N(CH$_3$)$_2$(+)—CH$_2$COO$^-$ or R—CO—NH—CH$_2$CH$_2$—N(CH$_3$)$_2$(+)—CH$_2$COO$^-$), obtained by the reaction of a monohaloacetate salt (e.g., sodium monochloroacetate) with the reaction product of either dimethyl amino propylamine or dimethyl amino ethylamine with a suitable carboxylic acid or ester derivatives thereof, such as $C_{10}$-$C_{18}$ amidopropyl dimethylamino betaine;

$C_6$-$C_{22}$ alkyl sultaines or $C_6$-$C_{22}$ alkyl amido sultaines, which are similar to those $C_6$-$C_{22}$ alkyl dialkyl betaines or $C_6$-$C_{22}$ alkyl amido betaines described above except in which the carboxylic group has been substituted by a sulfonic group (R—N(CH$_3$)$_2$(+)—CH$_2$CH$_2$CH$_2$SO$_3^-$ or R—CO—NH—CH$_2$CH$_2$CH$_2$—N(CH$_3$)$_2$(+)—CH$_2$CH$_2$CH$_2$SO$_3^-$ or R—CO—NH—CH$_2$CH$_2$—N(CH$_3$)$_2$(+)—CH$_2$CH$_2$CH$_2$SO$_3^-$) or a hydroxysulfonic group (R—N(CH$_3$)$_2$(+)—CH$_2$CH(OH)—CH$_2$SO$_3^-$ or R—CO—NH—CH$_2$CH$_2$CH$_2$—N(CH$_3$)$_2$(+)—CH$_2$CH(OH)—CH$_2$SO$_3^-$ or R—CO—NH—CH$_2$CH$_2$—N(CH$_3$)$_2$O—CH$_2$CH(OH)—CH$_2$SO$_3^-$), such as $C_{10}$-$C_{18}$ dimethyl hydroxysultaine and $C_{10}$-$C_{18}$ amido propyl dimethylamino hydroxysultaine;

and mixtures thereof.

Contacting

The fluid sample may be contacted with the solution to form the mixture using any method known to those of ordinary skill in the art. For example, the fluid sample may be added to the solution, or the solution may be added to the fluid sample. After combining the fluid sample with the solution, the methods herein may involve manual stirring, mechanical stirring, shaking, blending, mixing, swirling, circulation techniques, sonication (e.g., ultrasonication), or any other agitation technique to form a mixture, preferably a homogenous mixture.

In some embodiments, the fluid sample is added to the solution as a single portion. Alternatively, the fluid sample may be added dropwise or portionwise (e.g., titrated) into the solution with concomitant agitation, whereby the UV-Vis absorption and/or fluorescence emission profile of the mixture is optionally measured subsequent to each drop/portion of the fluid sample added. Such a procedure may be employed, for example, when it is desired to determine a concentration of palladium ions in the fluid sample by generating a titration curve.

From such titration procedures, the rate constant of association for palladium ion can be determined. In some embodiments, the chemosensor of formula I has an observed palladium ion association rate constant of $8.1\times10^5 M^{-1}$ to $9.1\times10^5 M^{-1}$, preferably $8.2\times10^5 M^{-1}$ to $9.0\times10^5 M^{-1}$, preferably $8.3\times10^5 M^{-1}$ to $8.9\times10^5 M^{-1}$, preferably $8.4\times10^5 M^{-1}$ to $8.8\times10^5 M^{-1}$, preferably $8.5\times10^5 M^{-1}$ to $8.7\times10^5 M^{-1}$, preferably $8.5\times10^5 M^{-1}$ (Error estimated to be ≤10%). Thus extremely short contacting times may be used. In some embodiments, the solution (and thus the chemosensor of formula I) is contacted with the fluid sample for 1 second to 10 minutes, preferably 5 seconds to 8 minutes, preferably 10 seconds to 6 minutes, preferably 30 seconds to 4 minutes, preferably 1 minute to 2 minutes, prior to the measuring. Of course, longer or shorter contacting times may also be employed, as appropriate.

Mixture

The chemosensor of formula I may be employed in any quantity that provides an accurate UV-Vis absorption and/or fluorescence emission readout, which can be readily ascertained by one of ordinary skill in the art. Typically, a sufficient amount of the chemosensor of formula I is present in the solution to provide the mixture with a chemosensor of formula I concentration ranging from 0.1 to 20 µM, preferably 0.5 to 19 µM, preferably 1 to 18 µM, preferably 2 to 17 µM, preferably 3 to 16 µM, preferably 4 to 15 µM, preferably 5 to 14 µM, preferably 6 to 13 µM, preferably 7 to 12 µM, preferably 8 to 11 µM, preferably 9 to 10 µM, based on a total volume of the mixture. In general, the quantity of the chemosensor of formula I is selected to provide the mixture with a molar equivalence of the palladium ions to the chemosensor of formula I of from 0.01:1 to 20:1, preferably 0.05:1 to 18:1, preferably 0.1:1 to 16:1, preferably 0.5:1 to 14:1, preferably 1:1 to 12:1, preferably 1.5:1 to 10:1, preferably 2:1 to 8:1, preferably 4:1 to 6:1, although molar ratios above or below these values may also be utilized as needed.

Measurements

The detection of palladium ions in the fluid sample can be accomplished using ultraviolet visible (UV-Vis) absorption techniques, fluorescence emissions techniques, or both.

In some embodiments, after forming the mixture, an ultraviolet visible (UV-Vis) absorption profile of the mixture is measured to determine a presence or absence of palladium ions in the fluid sample. In some embodiments, the chemosensor of formula I has an ultraviolet visible absorption peak at 315 to 325 nm, preferably 317 to 323 nm, preferably 319 to 321 nm, preferably 320 nm in the absence of palladium (switched off), and, upon being exposed to palladium ions whereby a deallylation reaction occurs in the mixture, the deallylated chemosensor of formula IV is formed (switched on), which produces an ultraviolet visible absorption peak at 338 to 342 nm, preferably 339 to 341 nm, preferably 340 nm (a bathochromic shift).

Therefore, the presence of palladium ions in the fluid sample may be indicated by measuring or monitoring for the appearance of an absorption peak at 338 to 342 nm (e.g., 340 nm). If an absorption peak at 338 to 342 nm (e.g., 340 nm) exists in the ultraviolet visible (UV-Vis) absorption profile, then palladium ions are present in the mixture (and thus the fluid sample), and if no absorption peak at 338 to 342 nm (e.g., 340 nm) exists in the ultraviolet visible (UV-Vis) absorption profile, and only an absorption peak at 315 to 325 nm, (e.g., 320 nm) is present, then it can be determined that no palladium ions are present in the mixture (and thus the fluid sample).

In some embodiments, the method may first involve measuring or otherwise obtaining an ultraviolet visible absorption profile of the solution prior to contact with the fluid sample. Then after contacting with the fluid sample to form the mixture, the UV-Vis absorption profile of the mixture can be measured and directly compared to that obtained from the solution. Such a comparative analysis may advantageously provide accurate and reliable palladium ion detection.

In some embodiments, the method further involves determining/quantifying a concentration of the palladium ions in the fluid sample. This may be accomplished by measuring the absorbance ratio at 340 nm and 320 nm ($Abs_{340}/Abs_{320}$) of the mixture and comparing to a calibration curve that relates palladium ion concentration to the absorbance ratio at 340 nm and 320 nm ($Abs_{340}/Abs_{320}$). For example, an initial $Abs_{340}/Abs_{320}$ readout may be determined from the solution prior to contact with the fluid sample, then the fluid sample may be titrated into the solution to form the mixture, and the absorbance ratio at 340 nm and 320 nm ($Abs_{340}/Abs_{320}$) of the mixture may be measured after each addition to measure the ratiometric response. The concentration of palladium ions in the fluid sample may then be calculated by comparing a plot of $Abs_{340}/Abs_{320}$ as a function of concentration to a calibration curve formed using known concentrations of palladium ions, as is known to those of ordinary skill in the art.

Similarly, in some embodiments, after forming the mixture, a fluorescence emission profile of the mixture is measured at an excitation wavelength ($\lambda_{ex}$) of 330 nm to determine a presence or absence of palladium ions in the fluid sample. In some embodiments, the chemosensor of formula I has fluorescence emission peak of 380 to 400 nm, preferably 382 to 398 nm, preferably 384 to 396 nm, preferably 386 to 394 nm, preferably 388 to 392 nm, preferably 390 nm in the absence of palladium (switched off), and, upon being exposed to palladium ions whereby a deallylation reaction occurs in the mixture, the deallylated chemosensor of formula IV is formed (switched on), which produces a fluorescence emission peak at 530 to 550 nm, preferably 532 to 548 nm, preferably 534 to 546 nm, preferably 536 to 544 nm, preferably 538 to 542 nm, preferably 540 nm (a bathochromic shift).

Therefore, the presence of palladium ions in the fluid sample may be indicated by measuring or monitoring for the appearance of a fluorescence emission peak at 530 to 550 nm (e.g., 540 nm). If a fluorescence emission peak at 530 to 550 nm (e.g., 540 nm) exists in the fluorescence emission profile, then palladium ions are present in the mixture (and thus the fluid sample), and if no fluorescence emission peak at 530 to 550 nm (e.g., 540 nm) exists in the fluorescence emission profile, and only a fluorescence emission peak at 380 to 400 nm (e.g., 390 nm) is present, then it can be determined that no palladium ions are present in the mixture (and thus the fluid sample).

In some embodiments, the method may first involve measuring or otherwise obtaining a fluorescence emission profile of the solution prior to contact with the fluid sample. Then after contacting with the fluid sample to form the mixture, the fluorescence emission profile of the mixture can be measured and directly compared to that obtained from the solution. Such a comparative analysis may advantageously provide accurate and reliable palladium ion detection.

In some embodiments, the method further involves determining/quantifying a concentration of the palladium ions in the fluid sample. This may be accomplished by measuring a fluorescence intensity ratio at 540 nm and 390 nm ($I_{540}/I_{390}$) ($\lambda_{ex}$=330 nm) of the mixture and comparing to a calibration curve that relates palladium ion concentration to the fluorescence intensity ratio at 540 nm and 390 nm ($I_{540}/I_{390}$). For example, an initial $I_{540}/I_{390}$ readout may be determined on the solution prior to contact with the fluid sample, then the fluid sample may be titrated into the solution to form the mixture, and the fluorescence intensity ratio at 540 nm and 390 nm ($I_{540}/I_{390}$) may be measured after each addition to measure the ratiometric response. The concentration of palladium ions in the fluid sample may then be calculated by comparing a plot of $I_{540}/I_{390}$ as a function of concentration to a calibration curve formed using known concentrations of palladium ions, as is known to those of ordinary skill in the art.

The methods of the present disclosure are preferably selective for the detection of palladium ions, that is, only the presence of palladium ions in the mixture produces a bathochromic shift in the ultraviolet visible absorption profile and/or the fluorescence emission profile of the mixture. For example, cations other than palladium which may be present in the fluid sample, including but not limited to, cations of sodium, potassium, calcium, magnesium, strontium, rubidium, cesium, iron, cobalt, copper, nickel, zinc, cadmium, mercury, silver, aluminum, gallium, and lead, do not cause substantial deallylation of the chemosensor of formula I to occur (i.e., do not produce a bathochromic shift in either the ultraviolet visible absorption profile or the fluorescence emission profile of the mixture to an appreciable degree), even when present at 100-fold higher concentrations (or more) than palladium.

In some embodiments, non-palladium cations (e.g., one or more cations of sodium, potassium, calcium, magnesium, strontium, rubidium, cesium, iron, cobalt, copper, nickel, zinc, cadmium, mercury, silver, aluminum, gallium, and lead), when present in the mixture (10 molar equivalence relative to the chemosensor of formula I), preferably produce a fluorescence intensity ratio ($I_{540}/I_{390}$) ($\lambda_{ex}$=330 nm) of 0 to 0.1, preferably 0 to 0.08, preferably 0 to 0.06, preferably 0 to 0.05, preferably 0 to 0.04, preferably 0 to 0.03, preferably 0 to 0.02. Whereas palladium ions, when present in the mixture (10 molar equivalence relative to the chemosensor of formula I), preferably produce a fluorescence intensity ratio ($I_{540}/I_{390}$) of 70 to 80, preferably 71 to 79, preferably 72 to 78, preferably 73 to 77, preferably 74 to 76, preferably 75. The change in fluorescence intensity ratio ($I_{540}/I_{390}$) values between palladium cation and non-palladium cations (e.g., one or more cations of sodium, potassium, calcium, magnesium, strontium, rubidium, cesium, iron, cobalt, copper, nickel, zinc, cadmium, mercury, silver, aluminum, gallium, and lead) corresponds to a difference of roughly 2,500 fold, which enables extremely accurate and facile palladium ion detection and/or palladium ion concentration determination, even in the presence of various other cations.

Due to the size of bathochromic shift in the spectral bands, in particular the fluorescence emission peaks, and the chemodosimetric mechanism that is specific to palladium that causes such a large bathochromic shift, the chemosensor of formula I has been found to be an excellent sensor for the accurate and sensitive detection of palladium, without interference from other common cations found in environmental and/or biological fluid samples. Indeed, the methods herein may have a palladium ion detection lower limit of 40 to 60 ppb, preferably 41 to 58 ppb, preferably 42 to 56 ppb, preferably 43 to 54 ppb, preferably 44 to 52 ppb, preferably 45 to 50 ppb, preferably 46 to 49 ppb.

The examples below are intended to further illustrate protocols for preparing the chemosensor and for detecting palladium ions in fluid samples using the chemosensor, and are not intended to limit the scope of the claims.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

EXAMPLES

General Methods

Melting points were determined using a Thomas-Hoover capillary melting point apparatus and are uncorrected. $^1$H and $^{13}$C NMR spectra were recorded on a JEOL 400 MHz spectrometer using Me$_4$Si as the internal standard. UV-vis absorption spectra were obtained using a Jasco V-670 spectrophotometer. Fluorescence spectra were measured using a Horiba, Fluorolog-3 fluorescence spectrophotometer, equipped with a xenon discharge lamp and 1 cm quartz cells with slit width 5 nm. All of the measurements were carried out at 298 K.

Deionized water (double distilled) was used throughout the experiment as the aqueous media. All other materials used for synthesis and solvents were purchased from Aldrich Chemical Co. and used without further purification. Compound 4 was synthesized in accordance with the literature procedure. See Sivaraman G, Chellappa D (2013) J Mater Chem B 1: 5768-5772, incorporated herein by reference in its entirety. The solutions of metal ions were prepared from their nitrate and chloride salts (analytical grade), and subsequently diluted to prepare working solutions. HEPES buffer solutions at different pH values were prepared using appropriate amounts of HEPES and KOH (all of analytical grade) under adjustment by a Mettler Toledo pH meter.

Synthesis

Figure 6:
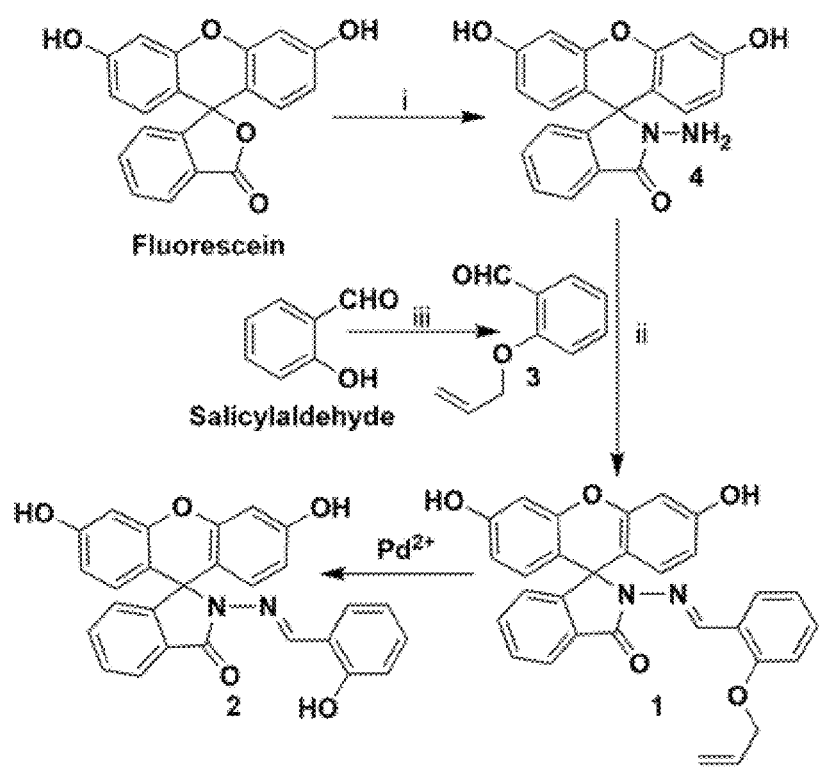
FIG. 6 illustrates the synthetic scheme and conditions for synthesizing compounds 1 and 2.

Chemosensor 1 (also referred to as compound 1), which is based on a fluorescein-allyloxy benzene scaffold, was synthesized according to the synthetic route shown in FIG. 6.

Synthesis of 3

A mixture of salicylaldehyde (250 mg, 2.0 mmol), allyl bromide (135 mg, 1.1 mmol), and potassium carbonate (275 mg, 2.0 mmol) in acetonitrile (10 mL) were refluxed for 12 h. The solvent was removed under vacuum and the residue was diluted with water and extracted with ethyl acetate. The organic layer was dried over anhydrous $Na_2SO_4$ and concentrated. The residue was purified by $SiO_2$ column chromatography (elution with EtOAc:hexane-1:4) to give 3 as pale yellow oil in 95% yield. $^1$H NMR (400 MHz, $CDCl_3$), δ (ppm): 4.62 (d, J=4.0 Hz, 2H), 5.30 (d, J=8.4 Hz, 1H), 5.42 (d, J=14.8 Hz, 1H), 6.0-6.1 (m, 1H), 6.94 (d, J=6.8 Hz, 1H), 6.99 (t, J=6.0 Hz, 1H), 7.49 (t, J=6.0 Hz, 1H), 7.80 (d, J=6.0 Hz, 1H), 10.5 (s, 1H). $^{13}$C NMR (100 MHz, $CDCl_3$), δ (ppm): 69.0, 113.1, 118.5, 120.5, 125.3, 128.0, 132.2, 136.1, 162.1, 189.2.

Synthesis of 1

Fluorescein hydrazide (4, 0.5 g, 1.4 mmol) and 3 (0.275 g, 1.7 mmol) were mixed in 10 mL of ethanol. The mixture was refluxed for 12 h with stirring, resulting in the formation of a yellow precipitate. The precipitate was separated by filtration and washed with 3×10 mL of ethanol. After drying, compound 1 was obtained as a yellowish solid in 90% yield. mp. 200-202° C. ($CH_2Cl_2$-hexane); $^1$H NMR (400 MHz, DMSO-$d_6$), δ (ppm): 4.51 (d, J=4.0 Hz, 2H), 5.32 (d, J=6.8 Hz, 1H), 5.34 (d, J=12.4 Hz, 1H), 5.94-6.01 (m, 1H), 6.45 (d, J=1.6 Hz, 1H), 6.46 (d, J=1.6 Hz, 1H), 6.50 (s, 1H), 6.52 (s, 1H), 6.66 (d, J=1.6 Hz, 2H), 6.93 (t, J=6.4 Hz, 1H), 6.98 (d, J=6.8 Hz, 1H), 7.1 (d, J=6.0 Hz, 1H), 7.32 (t, J=5.6 Hz, 1H), 7.57 (t, J=5.6 Hz, 2H), 7.63 (t, J=6.0 Hz, 1H), 7.93 (d, J=6.0 Hz, 1H), 8.96 (s, 1H), 9.92 (s, 2H). $^{13}$C NMR (100 MHz, DMSO-$d_6$), δ (ppm): 65.30, 69.01, 103.14, 103.34, 110.19, 112.88, 113.50, 117.44 117.87, 121.30, 123.16, 123.68, 124.08, 125.19, 128.23, 128.75, 129.47, 132.13, 133.59, 134.49, 135.05, 142.80, 143.00, 151.62, 152.37, 157.11, 157.41, 159.08, 164.29 (FIG. S1 and S2). Anal Calcd for 1, $C_{30}H_{22}N_2O_5$: C, 73.46; H, 4.52; N, 5.71, Found: C, 73.35; H, 4.50; N, 5.62.

Synthesis of 2

Compound 1 (0.590 g, 1.2 mmol) and $PdCl_2$ (0.250 g, 1.4 mmol) were mixed in 10 mL of acetonitrile. The mixture was stirred for 1 h resulting in the formation of a yellowish precipitate. The precipitate was separated by filtration and washed with 3×10 mL of water. After drying, a yellowish solid in 95% yield was obtained. mp. 325-327° C. (MeOH-hexane); $^1$H NMR (400 MHz, DMSO-$d_6$), δ (ppm): 6.48 (d, J=2.4 Hz, 1H), 6.50 (d, J=2.0 Hz, 1H), 6.53 (s, 1H), 6.55 (s, 1H), 6.68 (d, J=2.0 Hz, 2H), 6.79-6.83 (m, 2H), 7.15 (d, J=6.8 Hz, 1H), 7.22 (t, J=7.6 Hz, 1H), 7.33 (d, J=8.0 Hz, 1H), 7.59-7.67 (m, 2H), 7.94 (d, J=6.4 Hz, 1H), 9.20 (s, 1H), 9.97 (s, 2H), 10.32 (s, 1H). $^{13}$C NMR (100 MHz, DMSO-$d_6$), δ (ppm): 63.91, 109.27, 112.88, 116.31, 118.18, 118.81, 119.24, 119.82, 121.31, 123.16, 123.68, 128.23, 128.75, 129.06, 130.11, 132.13, 134.49, 136.53, 150.63, 150.72, 151.62, 152.38, 157.11, 159.08, 161.22, 164.29 (FIG. S3 and S4). Anal Calcd for 2, $C_{27}H_{18}N_2O_5$: C, 71.99; H, 4.03; N, 6.22, Found: C, 71.88; H, 4.00; N, 6.15.

Results and Discussion

Compound 1 was prepared by the conjugation of allyloxy benzaldehyde with fluorescein hydrazide to get a Schiff base in which the excited state intramolecular proton transfer (ESIPT) is inhibited by the allyloxy group. Compound 1 was prepared by the reaction of 4 with 2-(Allyloxy) benzaldehyde 3, which in turn is obtained by the allylation of Salicylaldehyde in acetonitrile. Further deallylation of 1 results in the formation of 2 (FIG. 6). Both compounds 1 and 2 were prepared in good yields and their structures were confirmed using $^1$H, $^{13}$C NMR, and elemental analysis. In the $^1$H NMR the singlet peak at δ 8.96 and 9.19 ppm corresponds to the formation of imine =C-H proton for compounds 1 and 2 respectively. Compound 1 could be easily distinguished from 2 due to the presence of the doublet peaks at 4.51, 5.32, and 5.34 ppm and a multiplet peak at 5.94-6.01 ppm for the allyl group and the absence of the phenolic peak at 10.3 ppm. The characteristic hydroxyl protons of the fluorescein group appeared as a singlet at S 9.91 and 9.97 ppm for 1 and 2 respectively.

Figure 1B:
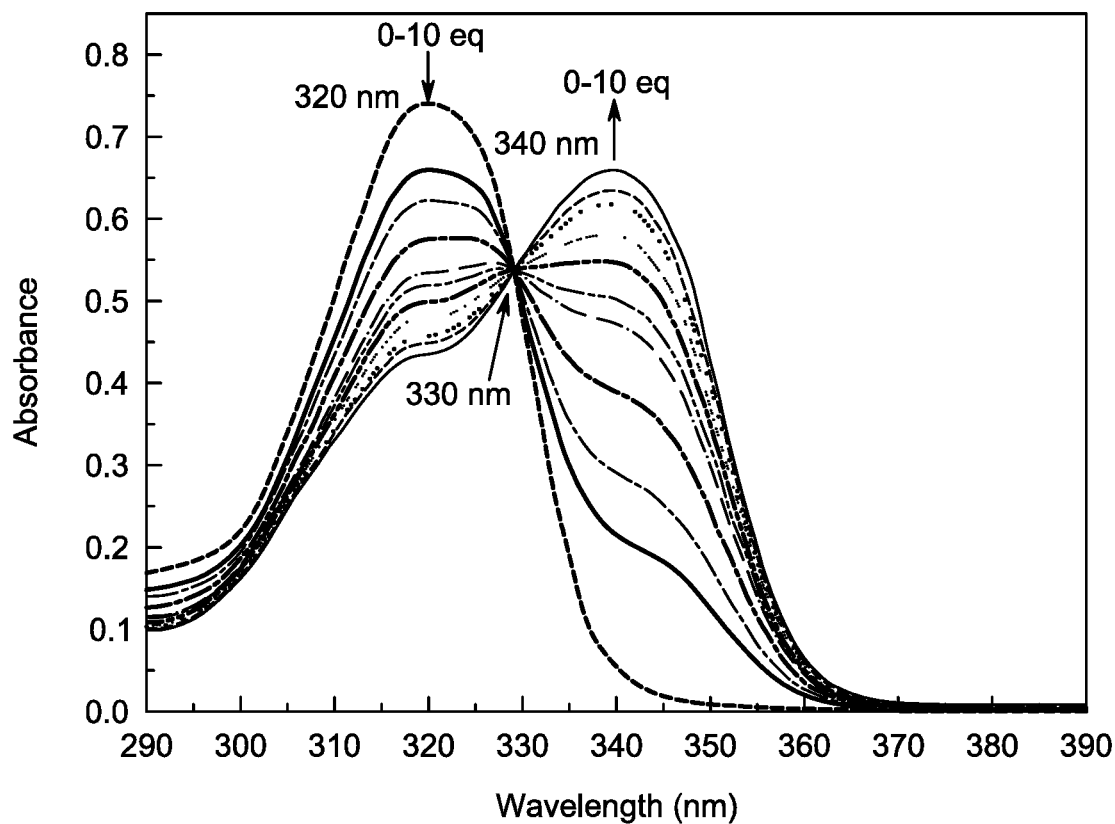
Figure 1C:
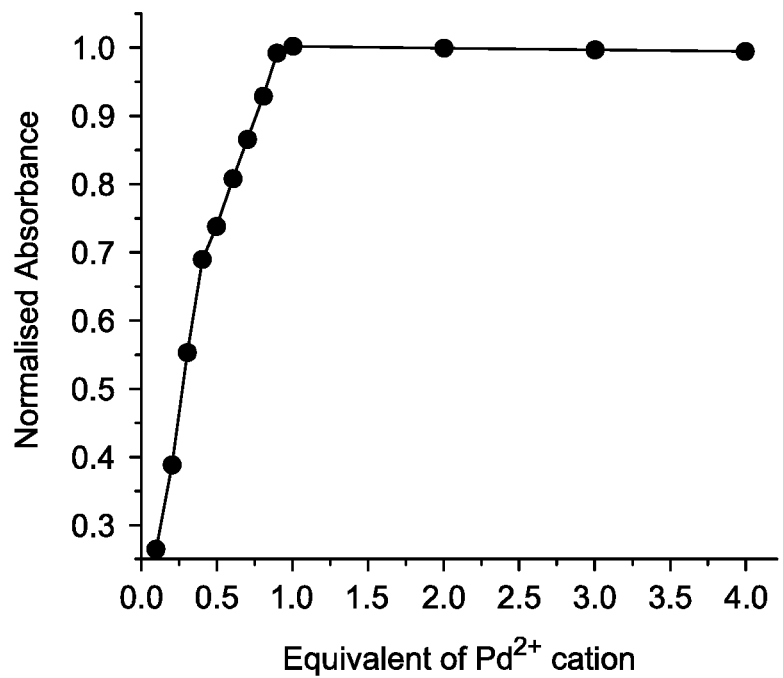

All the UV-vis absorption and fluorescence emission studies were carried out at a concentration of 10 μM and 1.0 μM in a mixed aqueous solution of water and DMF (9:1) containing HEPES buffer (10 mM, pH 7.4) respectively. The chemosensor 1 exhibited an absorption peak at 320 nm, which is attributed to the absorption of the xanthene moiety. See Yin W, Zhu H, Wang R (2014) Dyes Pigments 107: 127-132; and Zheng H, Zhan X-Q, Biana Q-N, Zhanga X-J (2013) Chem Commun 49: 429-447, each incorporated herein by reference in their entirety. Since, there was no apparent absorption band in the visible region it is assumed that chemosensor 1 exists in the lactam form in the mixed aqueous solution. However, upon the addition of $Pd^{2+}$ into the solution of 1, a new red-shifted absorption band at 340 nm is gradually increased, while the absorption band at 320 nm is decreased simultaneously with an isobestic point at 330 nm as shown in FIG. 1B. The peak at 340 nm is attributed to the deallylation of the conjugated phenol ring by the $Pd^{2+}$ species. The absorption bands at 340 nm increased linearly, up to 1 equivalent of $Pd^{2+}$ (FIG. 1C). The observed absorption response was selective for only $Pd^{2+}$ ions while the addition of other common metals cations (10 equiv), such as the transition metals, as well as alkali and alkaline earth metals, produce minimal or no considerable spectral changes (FIG. 1A).

Figure 2A:
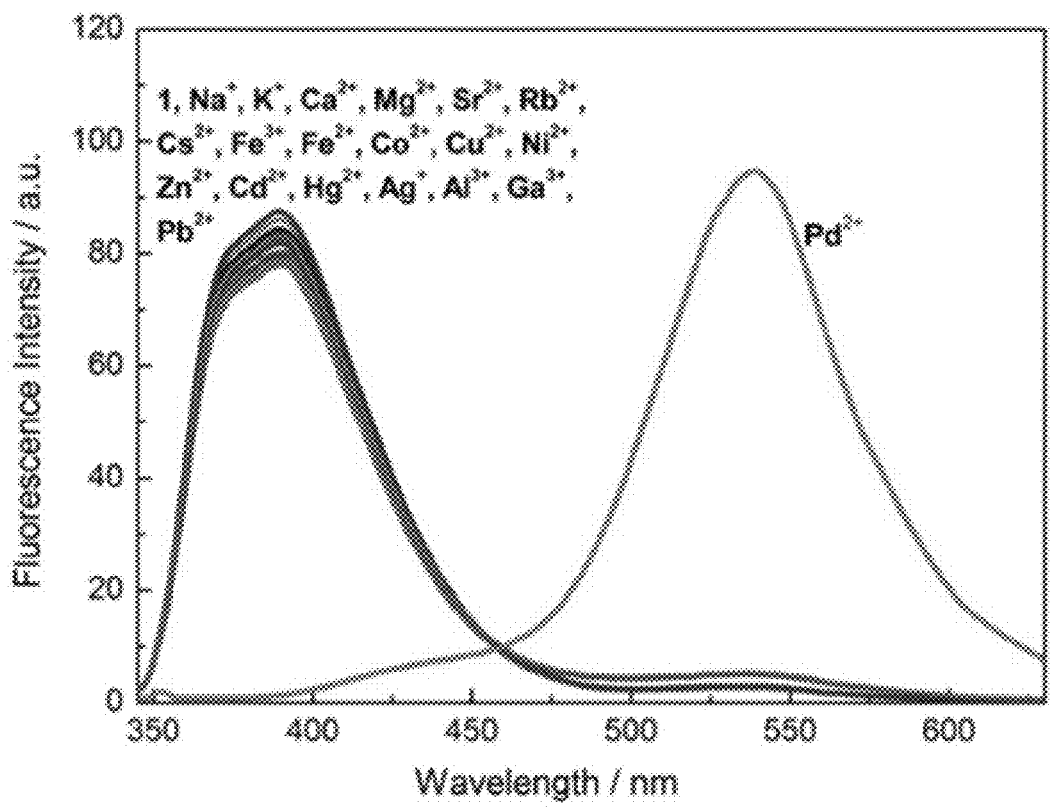
FIGS. 2A-2D illustrate the fluorescence spectra/properties of 1 (1.0 μM) with different cations (10 equivalents) (FIG. 2A), as a change from blue (no palladium) to yellow (with Pd$^{2+}$) fluorescence upon illumination at 365 nm (FIG. 2B), as a function of added PdCl$_2$ in different equivalence (up to 10 μM) in H$_2$O:DMF (9:1) containing HEPES buffer (10 mM, pH 7.4) ($\lambda_{ex}$=330 nm) (FIG. 2C), and as a mol ratio (equiv. Pd$^{2+}$) plot of emission at 390 and 540 nm (FIG. 1D)
Figure 2B:
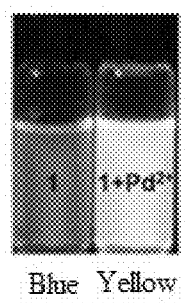
Figure 2C:
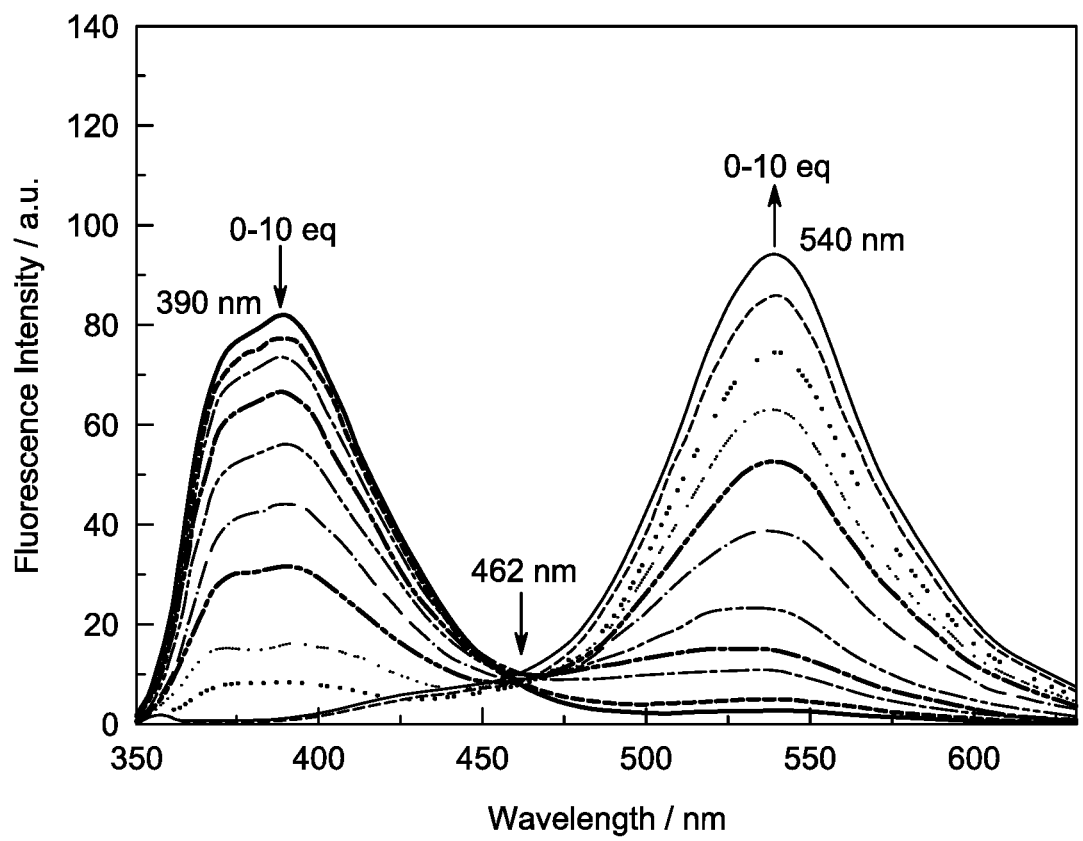
Figure 2D:
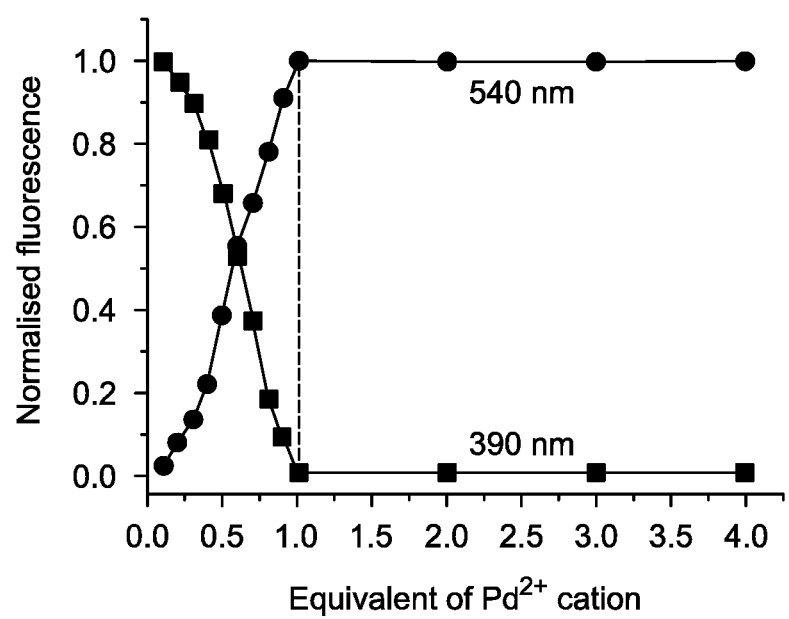
Figure 3:
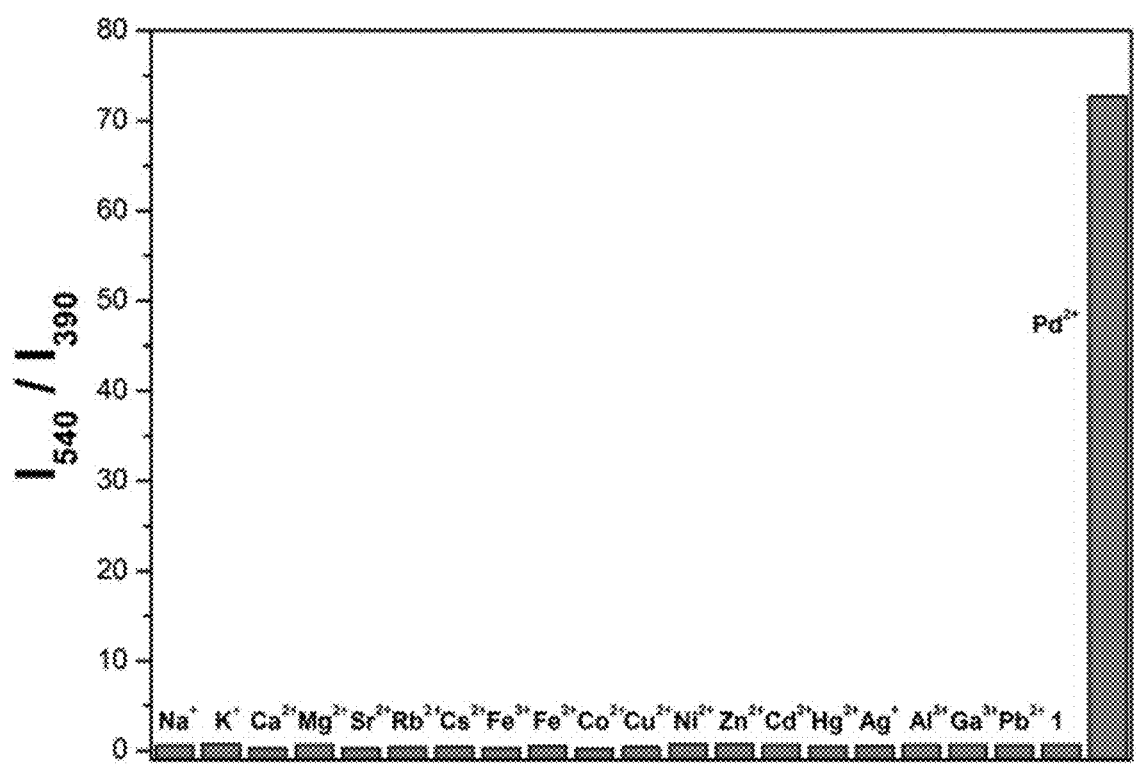
FIG. 3 illustrates the fluorescence intensities ratio ($I_{540}/I_{390}$) of 1 (1.0 μM) with different cations (10 equivalents) in H$_2$O:DMF (9:1) containing HEPES buffer (10 mM, pH 7.4). ($\lambda_{ex}$=330 nm)

Emission properties of chemosensor 1 were investigated by studying the complexation abilities of 1(1.0 μM) with 10 equiv of various biologically and non-biologically relevant metal cations in a mixed aqueous solution of water and DMF (9:1) with fluorescence emission. Chemosensor 1 on the addition of $Pd^{2+}$ produced a drastic red-shift of 150 nm from 390 nm to 540 nm with a fluorogenic change from blue to yellow fluorescence (FIG. 2A and 2B). None of the other cations except $Pd^{2+}$ produced such a distinct emission shift on interaction with 1 (FIG. 2A). In fluorescence titrations of 1 the emission peak at 390 nm, on slow addition of $Pd^{2+}$, decreased synchronously with the development of a new peak at 540 nm, with an isoemission point at 462 nm and a remarkable bathochromic shift of 150 nm (FIG. 2C). Thus the peak at 390 nm of chemosensor 1 was completely switched off while a new peak at 540 nm was switched on, by the interaction with $Pd^{2+}$ making it a potential ratiometric chemosensor. The peaks at 540 and 390 nm show a linear enhancement and diminution respectively with the increase of palladium ion concentration until it reaches 1 equivalent after that increase in $Pd^{2+}$ ion concentration did not lead to any further emission enhancement (FIG. 2D) which shows that only one equivalent of $Pd^{2+}$ interacts with one equivalent of the chemosensor 1. From the fluorescence titration, the rate constant for palladium ion was observed to be $8.6 \times 10^5$ $M^{-1}$ (Error estimated to be <10%). See Thordarson P (2011) Chem Soc Rev 40: 1305-1323, incorporated herein by reference in its entirety. The ratio of fluorescence intensities ($I_{540}/I_{390}$) ($\lambda_{ex}$=330 nm) changed from 0.03 to 75.7 (R=2523-fold) with a detection limit of 49 ppb. See Zhu B, Zhang X, Li Y, Wang P, Zhang H, Zhuang X (2010) Chem Commun 46: 5710-5712, incorporated herein by reference in its entirety. The ratio of fluorescence intensities ($I_{540}/I_{390}$) ($\lambda_{ex}$=330 nm) with different cations were also found to vary from 0.3 to 72.7 (FIG. 3). The fluorescence quantum yield calculated for 1 is 0.12 and after interaction with the one equivalent of $Pd^{2+}$ fluorescence quantum yield was found to be 0.25 under identical conditions.

In order to study the mechanism of fluorescence we isolated the product 2 formed on the interaction of 1 with $Pd^{2+}$ (FIG. 6). The $^1H$ and $^{13}C$ NMR of 2 showed that it is formed by the deallylation of 1 with $Pd^{2+}$ which is confirmed by disappearance of the allyl peaks and the presence of the phenolic proton peak in $^1H$ NMR. The fluorescein moiety has no absorption in the visible region and is weakly fluorescent in solution due to the preponderance of the ring-closed spirolactam form, which is evident by $^{13}C$ NMR signals at δ 65.3 and δ 63.9 ppm for compounds 1 and 2, respectively. See Egawa T, Koide Y, Hanaoka K, Komatsu T, Teraia T, Nagano T (2011) Chem Commun 47: 4162-4164; and Ueno T, Urano Y, Setsukinai K, Takakusa H Kojima H, Kikuchi K, Ohkubo K, Fukuzumi S, Nagano T (2004) J Am Chem Soc 126: 14079-14085, each incorporated herein by reference in their entirety. The blue fluorescence in 1 arises due to the electron transfer (ET) phenomenon from allyloxy benzene to the fluorescein ring. Deallylation of 1 with $Pd^{2+}$ restores the ESIPT of the phenolic group that assist the electron transfer (ET) phenomenon resulting in a drastic ratiometric change in the emission. See Kumar A, Kim H-S (2015) Spectrochim Acta A 148: 250-254; Helal A, Kim H-S, Yamani Z H, Shaikh M N (2016) J Fluoresc 26: 1-9; Kumar A, Kim H-S (2015) New J Chem 39: 2935-2942; Hens A, Maity A, Rajak K K (2014) Inorg Chim Acta 423: 408-420; Kavallieratos K, Rosenberg J M, Chen W-Z, Ren T (2005) J Am Chem Soc 127: 6514-6515; and Santra M, Roy B, Ahn K H (2011) Org Lett 13: 3422-3425, each incorporated herein by reference in their entirety.

Figure 4:
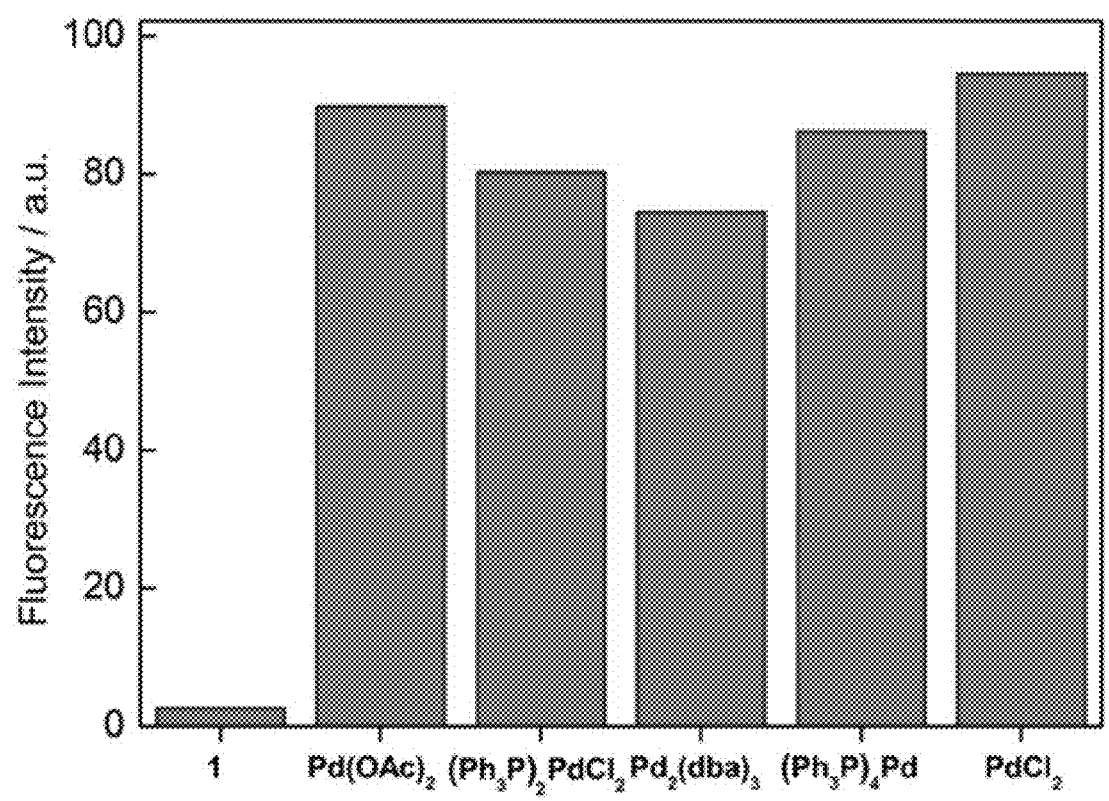
FIG. 4 illustrates the comparison of the fluorescence change depending on different palladium complexes, measured for an equimolar mixture of chemosensor 1 (1.0 μM) and the palladium species in H$_2$O:DMF (9:1) containing HEPES buffer (10 mM, pH 7.4). ($\lambda_{ex}$=330 nm)

The specific ratiometric response of chemosensor 1 towards $Pd^{2+}$ was further confirmed by a competitive binding experiment in the presence of transition metals, alkali and alkaline earth metals. These coexisting cations did not interfere with the ratiometric response to $Pd^{2+}$, even though their concentrations were 100-fold greater than the $Pd^{2+}$ concentration. Next, the fluorescence response of chemosensor 1 toward several typical palladium species such as $PdCl_2$, $Pd(PPh_3)_4$, $Pd(OAc)_2$, $PdCl_2(PPh_3)_2$, and $Pd_2(dba)_3$ was also examined. Chemosensor 1 responded to most commonly used species of palladium and exhibits significant ratiometric change in the emission. Thus this chemosensor can be used successfully for the sensing of different palladium species (FIG. 4).

Figure 5:
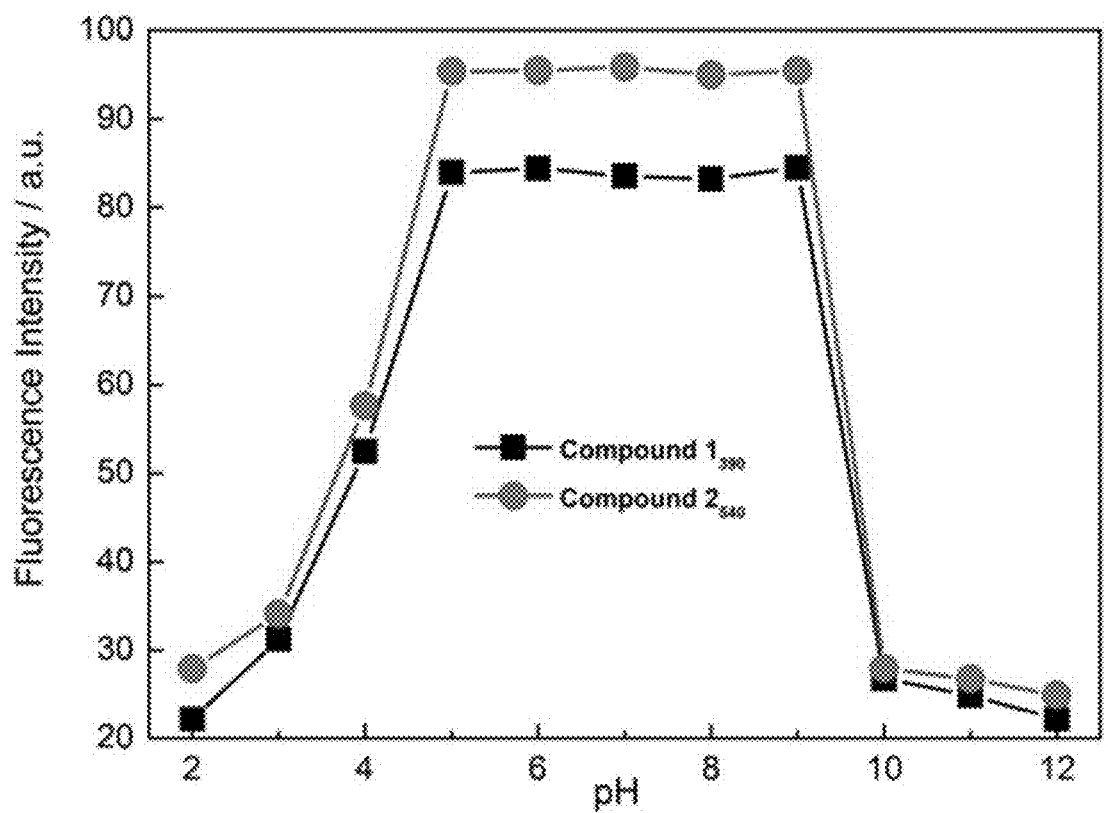
FIG. 5 illustrates the effect of pH on the emission intensities of 1 and 2, in H$_2$O:DMF (9:1) containing HEPES buffer (10 mM, pH 7.4). ($\lambda_{ex}$=330 nm)

For physiological and environmental applications, chemosensors should operate in a broad range of pH. In order to explain the effects of pH, the emission intensities of 1 and 2 were examined in the pH range of 2.0-12.0 (FIG. 5). Fluorescein exists in a colorless, non-fluorescent, and closed spirocyclic form at neutral and basic pH. In both 1 and 2 decreasing the pH value leads to the protonation of the oxygen of the allyloxy benzene or the phenol ring and this inhibits the ET to fluorescein, resulting in diminution of fluorescence. Compounds 1 and 2 showed maximum fluorescence intensities from pH 5.0 to 9.0. At higher pH values (>9.0), the fluorescence intensity decreased due to the increase of negative charge density on the allyloxy benzene or the phenol ring and subsequent formation of phenolate on the fluorescein core.

Thus, a new highly efficient, chemodosimetric, ratiometric chemosensor (1) based on a fluorescein-allyloxy benzene conjugate for $Pd^{2+}$ sensing has been developed. It was found that 1 produced a remarkably large (150 nm) bathochromic shift in emission upon deallylation with $Pd^{2+}$ to form 2, with an "on-off" type fluoroionophoric switching property. This behavior was identical with different species of palladium and within a pH range of 5.0-9.0. The detection limit for the chemosensor 1 for palladium was found to be 49 ppb and a rate constant of $8.6 \times 10^5$.

What is claimed is:

1. A method of detecting palladium ions in a fluid sample, comprising:
   contacting the fluid sample with a solution comprising water and a chemosensor to form a mixture; and
   measuring an ultraviolet visible absorption profile and/or a fluorescence emission profile of the mixture to determine a presence or absence of palladium ions in the fluid sample;
   wherein the chemosensor is of formula I

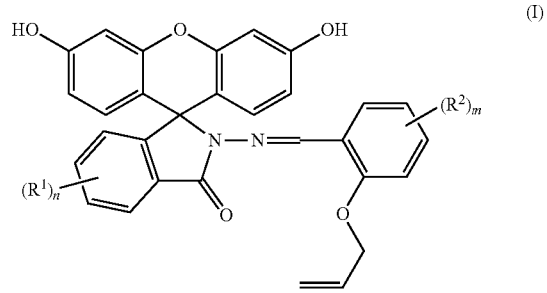

wherein:
each $R^1$ is independently an optionally substituted alkyl, an optionally substituted alkoxy, a carboxy, a disubstituted amino, an alkanoylamino, an amido, or an isothiocyano,
each $R^2$ is independently an optionally substituted alkyl, an optionally substituted aryl, an optionally substituted alkoxy, an alkanoyloxy, an optionally substituted alkoxycarbonyl, a halo, a substituted amino, a nitro, a cyano, or an azo,
n is 0 to 2, and
m is 0 to 4.

2. The method of claim 1, wherein n +m is equal to 0 to 2.

3. The method of claim 1, wherein
n is 0, or
n is 1 and $R^1$ is an optionally substituted alkyl or an optionally substituted alkoxy.

4. The method of claim 1, wherein
m is 0, or
m is 1 and $R^2$ is an optionally substituted alkyl, an optionally substituted alkoxy, or a halo.

5. The method of claim 1, wherein the chemosensor of formula I is

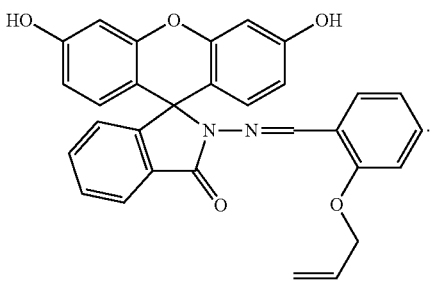 [SMILES: C=CCOc1ccccc1C=NN1C(=O)c2ccccc2C12c1ccc(O)cc1Oc1cc(O)ccc12]

6. The method of claim 1, wherein the chemosensor of formula I is present in the mixture at a concentration of 0.1 to 20 μM, based on a total volume of the mixture.

7. The method of claim 1, wherein palladium ions are present in the fluid sample, and wherein a molar equivalence of the palladium ions to the chemosensor of formula I in the mixture is from 0.05:1 to 20:1.

8. The method of claim 1, wherein the solution further comprises an organic solvent, and a ratio of water to the organic solvent in the solution is from 5:1 to 20:1.

9. The method of claim 1, wherein the solution further comprises 1 to 50 mM of a buffer, based on a total volume of the solution, and wherein the mixture has a pH of 5 to 9.

10. The method of claim 9, wherein the buffer is 4-(2-hydroxyethyl)-1-piperazineethanesulfonic acid.

11. The method of claim 1, wherein the fluid sample comprises greater than 55% v/v of water, and wherein the fluid sample is an industrial wastewater or a bodily fluid.

12. The method of claim 1, wherein the solution is contacted with the fluid sample for 1 second to 10 minutes prior to the measuring.

13. The method of claim 1, wherein the chemosensor of formula I has an ultraviolet visible absorption peak at 315 to 325 nm and a fluorescence emissions peak at 380 to 400 nm in the solution, and wherein a bathochromic shift in the ultraviolet visible absorption peak to 338 to 342 nm in the mixture and/or a bathochromic shift in the fluorescence emissions peak to 530 to 550 nm in the mixture indicates the presence of palladium ions in the fluid sample.

14. The method of claim 1, wherein the fluorescence emission profile of the mixture is measured, and the method further comprises determining a concentration of the palladium ions in the fluid sample by measuring a fluorescence intensity ratio of the mixture at 540 nm and 390 nm ($I_{540}/I_{390}$), and comparing to a calibration curve that relates palladium ion concentration to the fluorescence intensity ratio ($I_{540}/I_{390}$).

15. The method of claim 1, wherein the fluid sample comprises one or more cations of sodium, potassium, calcium, magnesium, strontium, rubidium, cesium, iron, cobalt, copper, nickel, zinc, cadmium, mercury, silver, aluminum, gallium, and lead.

16. The method of claim 15, which is selective for detection of palladium ions, wherein only the presence of palladium ions in the mixture produces a bathochromic shift in the ultraviolet visible absorption profile and/or the fluorescence emission profile of the mixture.

17. The method of claim 1, which has a palladium ion detection lower limit of 40 to 60 ppb.

18. A chemosensor of formula I,

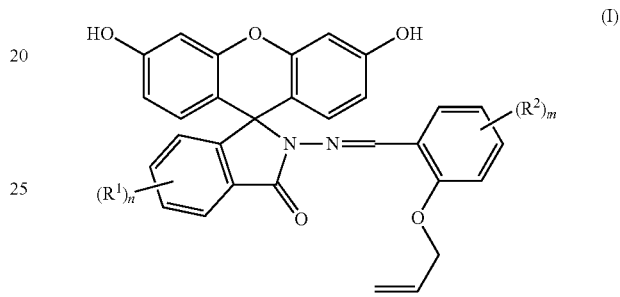

wherein:
each $R^1$ is independently an optionally substituted alkyl, an optionally substituted alkoxy, a carboxy, a disubstituted amino, an alkanoylamino, an amido, or an isothiocyano,
each $R^2$ is independently an optionally substituted alkyl, an optionally substituted aryl, an optionally substituted alkoxy, an alkanoyloxy, an optionally substituted alkoxycarbonyl, a halo, a substituted amino, a nitro, a cyano, or an azo,
n is 0 to 2, and
m is 0 to 4.

19. The chemosensor of claim 18, wherein n+m is equal to 0 to 2.

20. The chemosensor of claim 18, which is

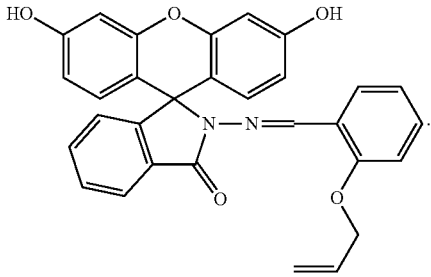 [SMILES: C=CCOc1ccccc1C=NN1C(=O)c2ccccc2C12c1ccc(O)cc1Oc1cc(O)ccc12]

* * * * *